(12) United States Patent
Olrik et al.

(10) Patent No.: US 7,998,028 B2
(45) Date of Patent: Aug. 16, 2011

(54) APPARATUS AND METHOD FOR PROVIDING A USER WITH A PERSONAL EXERCISE PROGRAM

(75) Inventors: Jakob Christian Olrik, Copenhagen (DK); Morten Green Hermansen, Copenhagen (DK); Tim Herbst, Copenhagen (DK); Henrik Duer, Copenhagen (DK); Eskild Ebbesen, Lyngby (DK); Alan Dickerson, Lyngby (DK); Soren Madsen, Bagsvaerd (DK); Henrik Schucany, Roskilde (DK)

(73) Assignee: Nokia Corporation, Espoo (FI)

( * ) Notice: Subject to any disclaimer, the term of this patent is extended or adjusted under 35 U.S.C. 154(b) by 0 days.

(21) Appl. No.: 12/890,507

(22) Filed: Sep. 24, 2010

(65) Prior Publication Data

US 2011/0151420 A1    Jun. 23, 2011

Related U.S. Application Data

(62) Division of application No. 10/986,468, filed on Nov. 10, 2004, now Pat. No. 7,883,445.

(51) Int. Cl.
*A63B 71/00* (2006.01)
(52) U.S. Cl. ............... 482/8; 482/1; 482/9; 482/901
(58) Field of Classification Search ............. 482/1–9, 482/51, 54, 57, 901–902; 434/247; 600/300, 600/301, 401, 595; 601/23
See application file for complete search history.

(56) References Cited

U.S. PATENT DOCUMENTS

| 6,659,916 B1 * | 12/2003 | Shea | 482/57 |
| 7,063,643 B2 * | 6/2006 | Arai | 482/8 |
| 2003/0134714 A1 * | 7/2003 | Oishi et al. | 482/6 |
| 2003/0171190 A1 * | 9/2003 | Rice | 482/57 |

* cited by examiner

*Primary Examiner* — Glenn Richman
(74) *Attorney, Agent, or Firm* — Ditthavong Mori & Steiner, P.C.

(57) ABSTRACT

A convenient device, such as a mobile phone, provides a user interface for a system that generated personalized exercise programs and guides users through the exercises in a generated program. The generation of the program may be performed by the device providing the user interface.

20 Claims, 30 Drawing Sheets

| 1 | 2 | 3 | 4 | 5 | 6 | 7 | 8 | 9 | 10 |
|---|---|---|---|---|---|---|---|---|---|
| b |   | a |   | b |   | a |   | c |    |

| 11 | 12 | 13 | 14 | 15 | 16 | 17 | 18 | 19 | 20 |
|----|----|----|----|----|----|----|----|----|----|
| b  |    | d  |    | a  |    | b  |    | c  |    |

| 21 | 22 | 23 | 24 | 25 | 26 | 27 | 28 | 29 | 30 |
|----|----|----|----|----|----|----|----|----|----|
| a  |    | a  |    | d  |    | b  |    | c  |    |

| 31 | 32 | 33 | 34 | 35 | 36 | 37 | 38 | 39 | 40 |
|----|----|----|----|----|----|----|----|----|----|
| b  |    | a  |    | a  |    | d  |    | c  |    |

Figure 22

ID
APPARATUS AND METHOD FOR PROVIDING A USER WITH A PERSONAL EXERCISE PROGRAM

RELATED APPLICATIONS

The present application is a divisional application of co-pending U.S. patent application Ser. No. 10/986,468, filed Nov. 10, 2004, incorporated herein its entirety for all purposes.

FIELD OF THE INVENTION

The present invention relates to an apparatus and method for providing a user with a personal exercise program.

BACKGROUND TO THE INVENTION

People follow exercise programs for a variety of reasons. These reasons include maintaining general well-being, assisting a weight loss program and preparation for a particular sporting event, such as a marathon. Such programs need to be carefully formulated if the desired effect is to be achieved and the exerciser is to avoid injury.

It is known, for example from U.S. Pat. No. 6,635,013, to use a computer to provide a user with an exercise program. However, this system merely provides printed static instructions. Consequently, a person who requires more interactive exercise program development must employ a personal fitness trainer which is inconvenient and costly.

SUMMARY OF THE INVENTION

It is an aim of the present invention to provide an apparatus and method for providing a fitness program which is cost-effective and convenient.

According to the present invention, there is provided an exercise assistance apparatus comprising user interface means and processing means configured for generating an exercise program on the basis of physical parameters of a user and controlling the user interface means to provide guidance to a user during performance of a program generated therefor.

Preferably, the apparatus includes input means for enabling the input physiological information, wherein the processing means is configured to determine an aerobic fitness value for a user in dependence on physiological information input using said input means.

Preferably, the processing means is configured such that said program comprises a plurality of exercise definitions, each including a variable exercise duration parameter, and the processing means is configured to set said variable parameter on the basis of physiological information input using the input means.

Preferably, said physiological information comprising information relating to aerobic fitness.

Preferably, the processing means is configured to calculate exercise duration by multiplying a base duration, defined in said program, by an aerobic fitness value for the user.

Preferably, the processing mean is configured to receive physiological information from the input means at the end of an exercise for which guidance has been provided and to modify said aerobic fitness value in dependence thereon.

Preferably, the processing means is configured for modifying said aerobic fitness at predetermined times. More preferably, said times are at intervals of 3 to 8 weeks.

Preferably, said modifying comprises determining an expected performance, determining actual performance from said physiological information received after exercises, comparing the expected and actual performances and increasing or decreasing said aerobic fitness value in dependence on the result of said comparison.

Preferably, the processing means is configured for generating an exercise program by selecting a mix of exercises of different intensity classes, the ratios of the mix of intensities being determined by said aerobic fitness value.

Preferably, the processing means is configured such that said ratios are additionally determined on the basis of the number of exercise sessions per week in the program being generated.

Preferably, the processing means is configured to select a varied selection of exercises in a class from a predetermined list of exercises.

Preferably, the exercises selected for a terminal period of said program represent an intensity reduction.

Preferably, the apparatus includes input means for enabling the input physiological information, wherein the processing means is configured to determine a strength value for a user in dependence on physiological information input using said input means.

Preferably, the processing means is configured for generating an exercise program by selecting exercises in dependence on said strength value.

Preferably, the processing means is configured such the selected exercises become successively harder during the program.

Preferably, the processing means is configured to select a varied selection of exercises from a predetermined list of exercises.

Preferably, the processing means is configured to generate an exercise program comprising both aerobic fitness and strength enhancing exercises.

Preferably, said processing means is comprised in a mobile phone.

Preferably, the input means comprises a wireless communication receiver.

Preferably, the apparatus includes monitoring means including means for deriving physiological information in respect of a person performing an exercise and wireless communication means for communicating derived physiological information to said wireless communication receiver.

According to the present invention, there is also provided a method of providing assistance to an exerciser comprising:
generating an exercise program on the basis of physical parameters of a user; and
controlling a user interface means to provide guidance to a user during performance of a program generated therefor.

Preferably, the method includes determining an aerobic fitness value for an exerciser in dependence on physiological information relating to said exerciser.

Preferably, said program comprises a plurality of exercise definitions, each including a variable exercise duration parameter, and said variable parameter is set on the basis of physiological information relating to said exerciser.

Preferably, said physiological information comprising information relating to aerobic fitness.

Preferably, exercise duration is calculated by multiplying a base duration, defined in said program, by an aerobic fitness value for the exerciser.

Preferably, the method comprises receiving physiological information at the end of an exercise for which guidance has been provided and modifying said aerobic fitness value in dependence thereon.

Preferably, said modifying of said aerobic fitness occurs at predetermined times. More preferably, said times are at intervals of 3 to 8 weeks.

Preferably, said modifying comprises determining an expected performance, determining actual performance from said physiological information received after exercises, comparing the expected and actual performances and increasing or decreasing said aerobic fitness value in dependence on the result of said comparison.

Preferably, the method comprises generating an exercise program by selecting a mix of exercises of different intensity classes, the ratios of the mix of intensities being determined by said aerobic fitness value.

Preferably, said ratios are additionally determined on the basis of the number of exercise sessions per week in the program being generated.

Preferably, a varied selection of exercises in the same class is selected from a predetermined list of exercises in a plurality of classes.

Preferably, the exercises selected for a terminal period of said program represent an intensity reduction.

Preferably, the method includes determining a strength value for a user in dependence on physiological information about the exerciser.

Preferably, an exercise program is generated by selecting exercises in dependence on said strength value.

Preferably, the selected exercises become successively harder during the program.

Preferably, the processing means is configured to select a varied selection of exercises from a predetermined list of exercises.

Preferably, the processing means is configured to generate an exercise program comprising both aerobic fitness and strength enhancing exercises.

According to the present invention, there is also provided an electrical or electromagnetic signal representing program codes for causing a computing device to operate so as to provide an apparatus according to the present invention.

According to the present invention, there is also provided a data carrier carrying a record of a signal according to the present invention.

BRIEF DESCRIPTION OF THE DRAWINGS

FIG. 22 shows an example of the aerobic exercise distribution of a weight control program.

DETAILED DESCRIPTION OF THE PREFERRED EMBODIMENTS

Embodiments of the present invention will now be described, by way of example, with reference to the accompanying drawings.

A first exemplary system, which embodies the present invention, will now be described.

Figure 1:
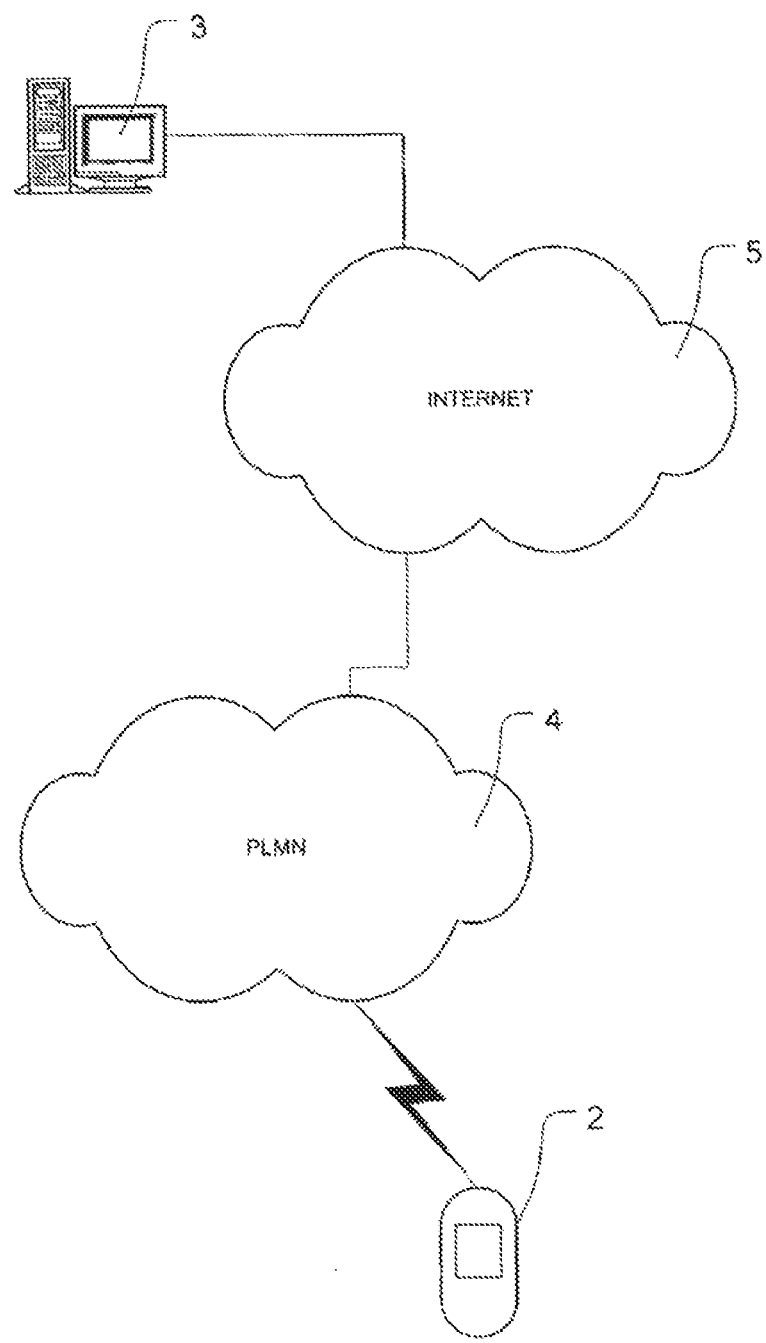
FIG. 1 shows the major components of a first exemplary system embodying the present invention.

Referring to FIG. 1, the first exemplary system comprises a mobile phone 2 and a server 3.

The mobile phone 2 can communicate with the server 3 via a mobile phone network 4 and the Internet 5 using XML messages and the HTTP protocol. The mobile phone 2 supports J2ME (Java 2 Micro Edition) MIDlets and the fitness program functions of the mobile phone 2 are implemented by a MIDlet.

The server 3 is a conventional HTTP server such as Apache.

Figure 2:
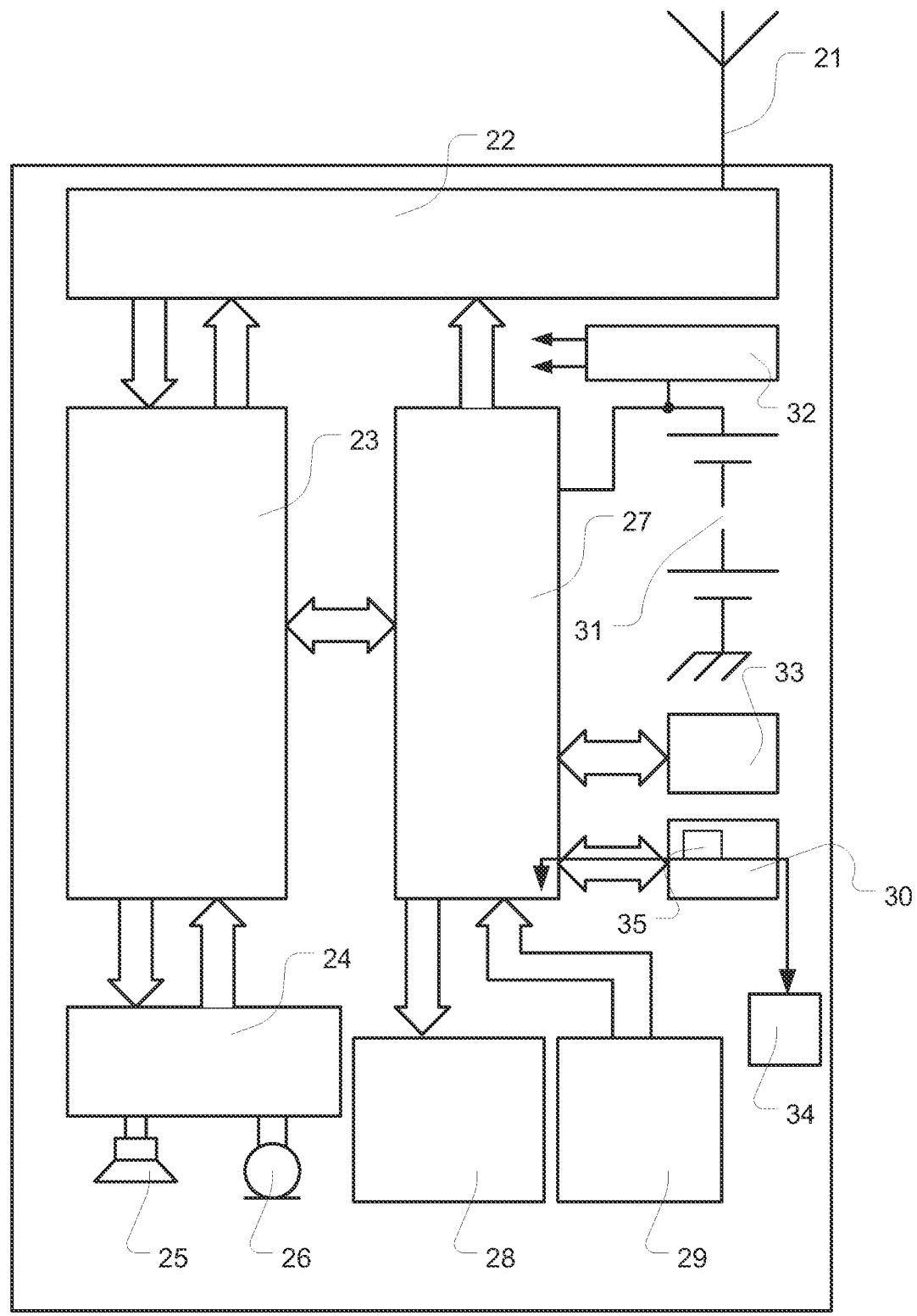
FIG. 2 is a block diagram of the mobile phone of FIG. 1.

Referring to FIG. 2, the mobile phone 2 comprises an antenna 21, an rf subsystem 22, a baseband DSP (digital signal processing) subsystem 23, an analog audio subsystem 24, a loudspeaker 25, a microphone 26, a controller 27, a liquid crystal display 28, a keypad 29, memory 30, a battery 31, a power supply circuit 32 and a SIM (subscriber identity module) 33 and an infrared transceiver 34.

The rf subsystem 22 contains the if and rf circuits of the mobile phone's transmitter and receiver and a frequency synthesizer for tuning the mobile phone's transmitter and receiver. The antenna 21 is coupled to the rf subsystem 22 for the reception and transmission of radio waves.

The baseband DSP subsystem 23 is coupled to the rf subsystem 22 to receive baseband signals therefrom and for sending baseband modulation signals thereto. The baseband DSP subsystems 23 includes codec functions which are well-known in the art.

The analog audio subsystem 24 is coupled to the baseband DSP subsystem 23 and receives demodulated audio therefrom. The analog audio subsystem 24 amplifies the demodulated audio and applies it to the loudspeaker 25. Acoustic signals, detected by the microphone 26, are pre-amplified by the analog audio subsystem 24 and sent to the baseband DSP subsystem 24 for coding.

The controller 27 controls the operation of the mobile phone 2. To this end, it is coupled to the rf subsystem 22 for supplying tuning instructions to the frequency synthesizer and to the baseband DSP subsystem for supplying control data and management data for transmission. The controller 27 operates according to a program stored in the memory 30 with reference to the contents of the SIM 33. The memory 30 is shown separately from the controller 27. However, it may be integrated with the controller 27.

The display device 28 is connected to the controller 27 for receiving control data and the keypad 29 is connected to the controller 27 for supplying user input data signals thereto.

The battery 31 is connected to the power supply circuit 32 which provides regulated power at the various voltages used by the components of the mobile phone. The positive terminal of the battery 31 is connected to an analog-to-digital converter (ADC) input of the controller 27.

Among the programs stored in the memory 30 is a Java virtual machine program that supports J2ME (Java 2 Micro Edition) MIDP (Mobile Information Device Profile) 2.0 programming of the mobile phone 2 and a fitness trainer MIDlet 35. The fitness trainer MIDlet 35 can generate an exercise program for a user, guide the user through the exercise program and adjust the program on the basis of the user's progress through an exercise program.

The fitness trainer MIDlet 35 will now be described in detail.

Figure 3:
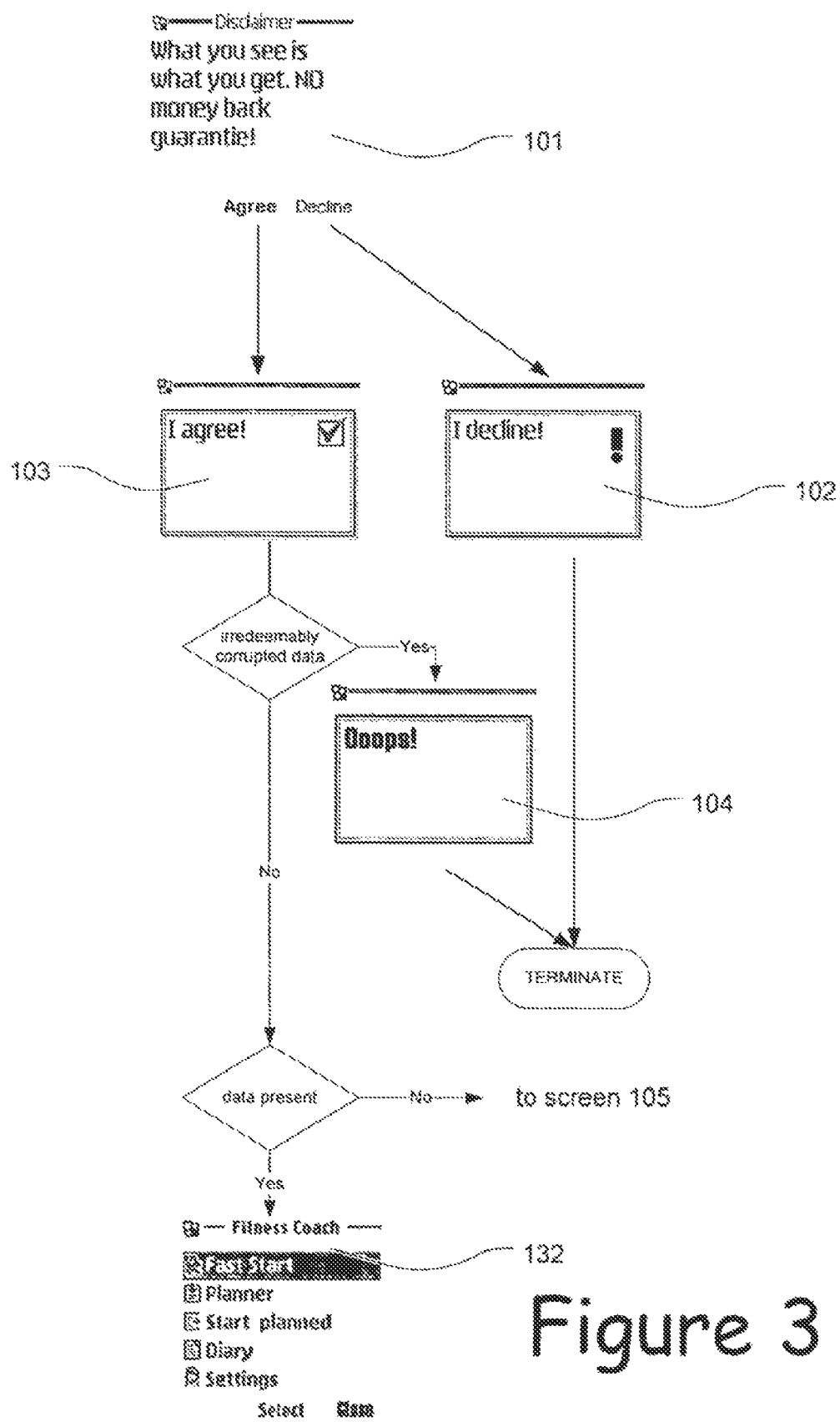
FIG. 3 illustrates the user interface of the MIDlet 35 during initialisation.
Figure 10:
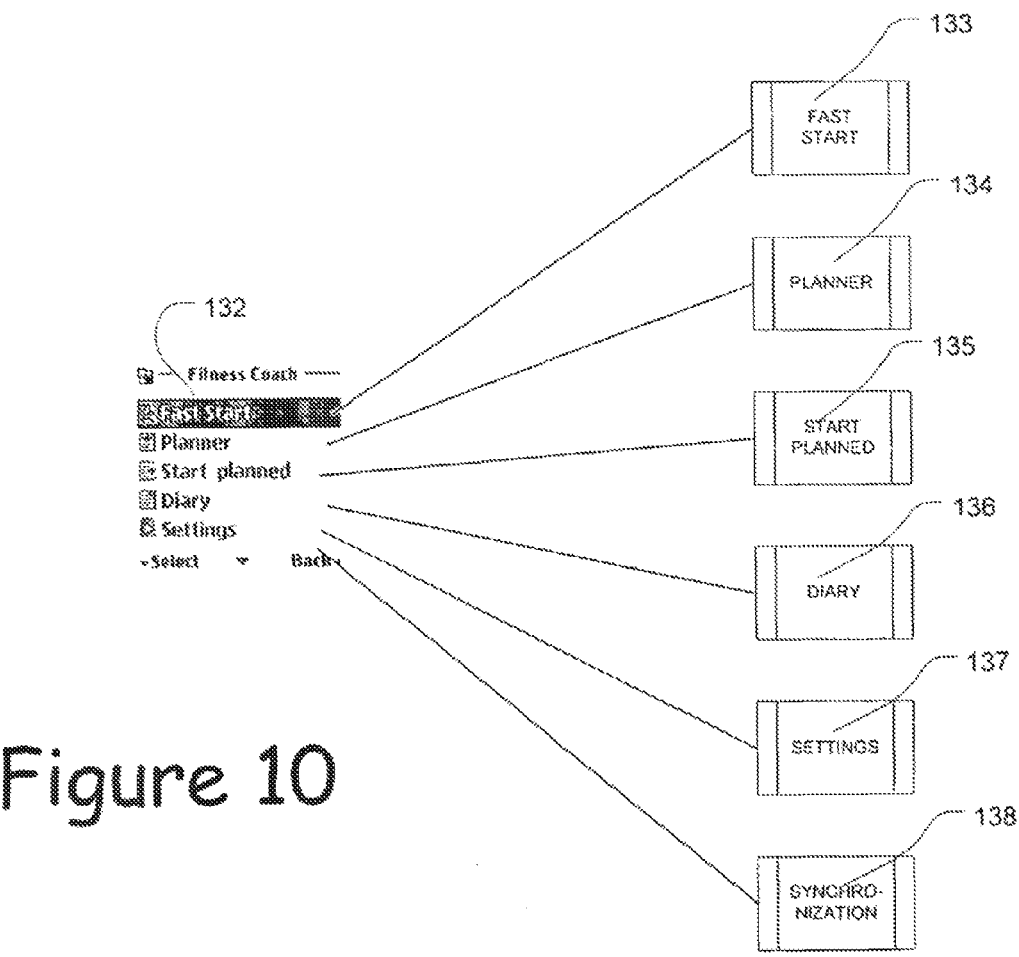
FIG. 10 illustrates the overall structure of the user interface of the MIDlet.

Referring to FIG. 3, when the user instructs the mobile phone 2 to execute the fitness trainer MIDlet, the MIDlet 35 is instantiated. During the instantiation of the MIDlet, the MIDlet 35 displays a screen 101 inviting the user to agree to the terms of usage of the MIDlet. If the user declines to accept the conditions by selecting a Decline command, a confirmatory screen 102 is displayed and the MIDlet 35 terminates. If the user accepts the terms by selecting an Agree command, the MIDlet 35 displays a confirmatory screen 103 and then attempts to read configuration data from a record store. If a record store seems to be present but contains corrupted data, the MIDlet 35 determines whether the record store memory is so corrupted that it is not even possible to identify the regions that relate to the MIDlet. In the case of severe corruption of the record store memory, the MIDlet 35 generates an error message screen 104 and destroys itself. If, on the other hand, the MIDlet's record store is identifiable but contains meaningless data, the MIDlet 35 clears the record store and the MIDlet 35 enters a set up process 137 (FIG. 10).

Similarly, if there is no record store, as would be the case when the MIDlet 35 is first executed on the mobile phone 2, or there is an empty record store, the MIDlet 35 enters the set up process 137.

Figure 4:
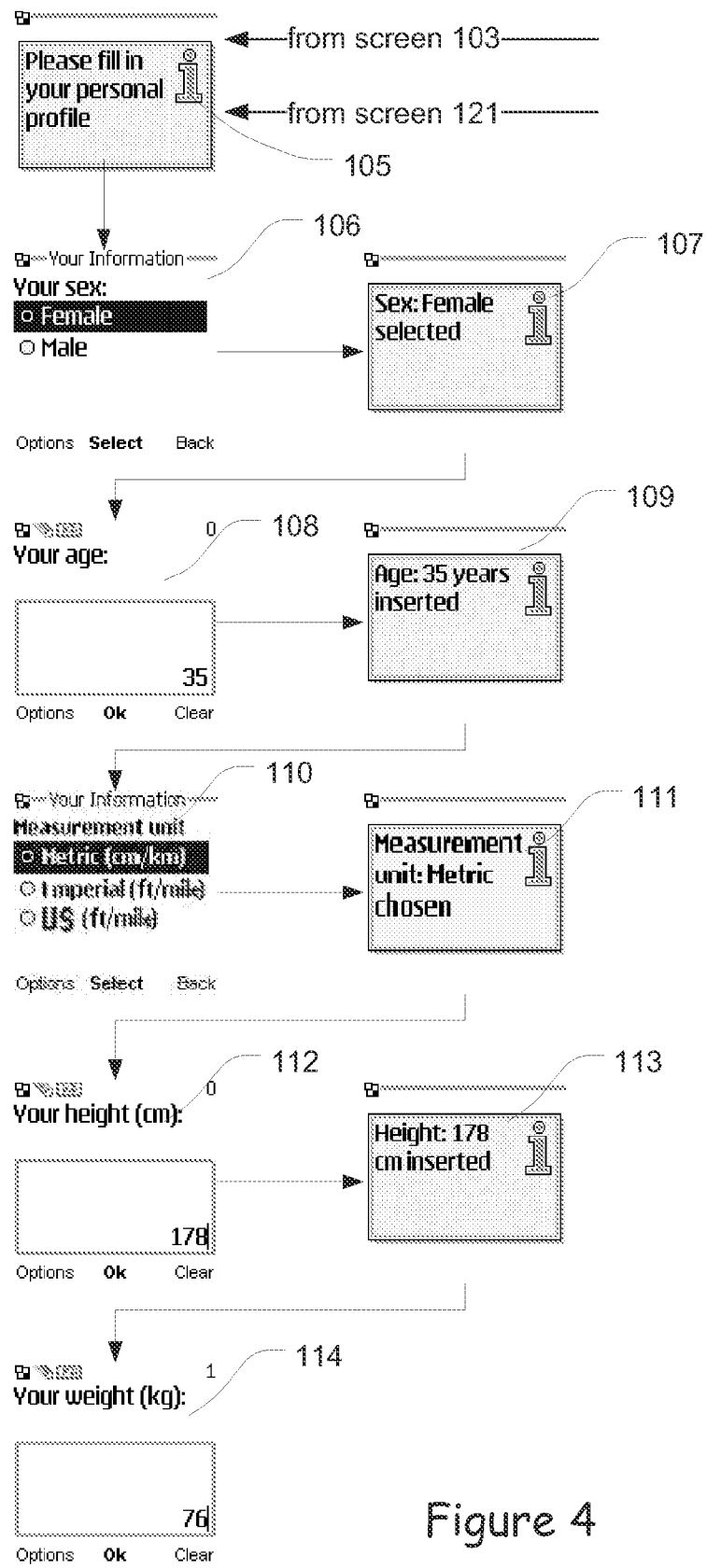
FIG. 4 illustrates the user interface of the MIDlet 35 for personal data entry.
Figure 4:
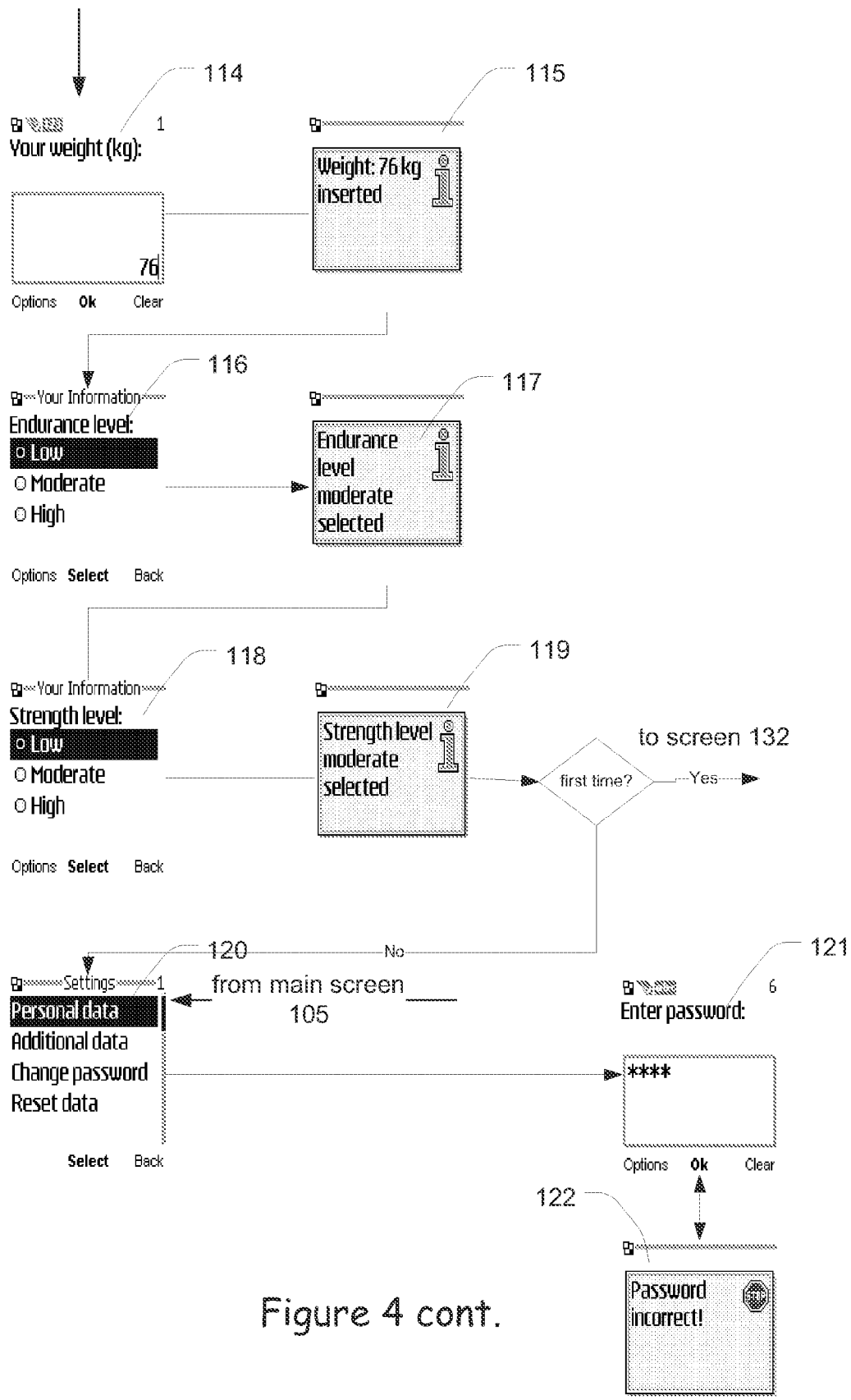

Referring to FIG. 4, when the MIDlet 35 enters the set up process, the MIDlet 35 displays an invitation screen 105 inviting the user to enter their detail for a short period. The user is then presented with a list screen 106 which enables the user to enter their gender. When the user has entered their gender by selecting the appropriate option in the list screen 106, the selection is confirmed in a gender confirmation screen 107.

The gender confirmation screen 107 is displayed for short period and is then replaced by an age input screen 108. When the user has input their age, an age confirmation screen 109 is displayed for a short period.

The age confirmation screen 109 is replaced by a measurement units list screen 110 which enables the user to select one of the metric, Imperial avoirdupois and US avoirdupois systems for display and input of lengths and weights. When the user has selected a system of units, a units confirmation screen 111 is displayed for a short period.

After the selected units have been confirmed, the user is presented with a height input screen 112. The height input screen 112 invites the user to input their height in units of the selected system of units, i.e. centimeters for metric and feet and inches for both avoirdupois systems. The input height is confirmed by a height confirmation screen 113 which is displayed for a short period.

After the input height has been confirmed, the user is presented with a weight input screen 114. The weight input screen 114 invites the user to input their weight in units of the selected system of units, i.e. kilograms for metric, stones and pounds for Imperial avoirdupois and pounds for US avoirdupois. The input weight is confirmed by a weight confirmation screen 115 which is displayed for a short period.

Non-metric height and weight values are converted into metric values for storage by the MIDlet 35. All calculations use the metric values, the non-metric values only being used for user interface purposes.

After the input weight has been confirmed, the user is presented with an endurance list screen 116 which enables the user to input their level of endurance (high, moderate and low). The user may obtain assistance in selecting the correct level by selecting a Help command from a menu revealed by selecting the options. Once the user has selected their endurance level, an endurance confirmation screen 117 is displayed for a short period.

After the input endurance has been confirmed, the user is presented with a strength list screen 118 which enables the user to input their level of strength (high, moderate and low). The user may obtain assistance in selecting the correct level by selecting a help option from the options menu. Once the user has selected their strength level, an endurance confirmation screen 119 is displayed for a short period.

The entered personal details are now saved to the MIDlet's record store and the settings process 137 is exited as this is the first time that it has been entered.

Referring to FIG. 10, when the MIDlet 35 has been loaded successfully, the user is presented with a main screen 132 which comprises a list of options consisting of Fast Start, Planner, Start Planned, Diary, Settings, Instructions and Synchronization.

If the user selects the Settings option, the MIDlet 35 clears the user's settings and performs the setting process 137.

Referring again to FIG. 4, the user is initially presented with a settings list screen 120, containing Personal Data, Additional Data, Change Password and Reset Data options, is displayed.

If the user selects the Personal Data option, a password entry screen 121 is displayed. The user must input a password, if it has been previously set, using the password entry screen 121. If the password is correct, the invitation screen 105 is shown and the user can proceed through screens 105 to 119 as described above. However, after screen 119, the user is returned to the settings list screen 120. If the password is not correctly entered, a password error screen 122 is displayed for a short period and the user is the presented with the password entry screen 121 again.

Figure 5:
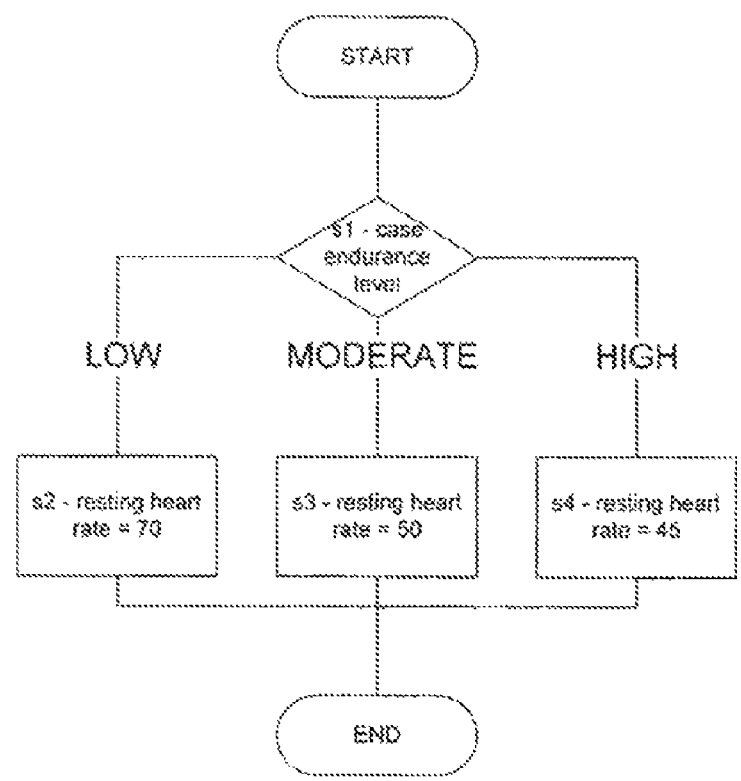
FIG. 5 is a flowchart illustrating a method of setting a resting heart rate.

A default resting heat rate is determined on the basis of the user's endurance level. Referring to FIG. 5, the entered endurance level is identified (step s1) and if the entered endurance level is LOW, the resting heart rate is set to 70 beats per minute (bpm) (step s2). If the entered endurance level is MODERATE, the resting heart rate is set to 50 bpm (step s3) and, if the entered endurance level is HIGH, the resting heart rate is set to 45 bpm (step s4).

Figure 6:
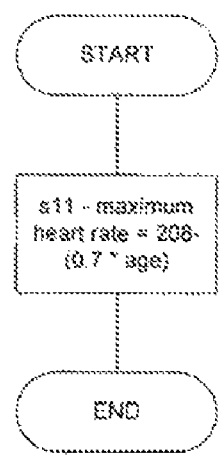
FIG. 6 is a flowchart illustrating a method of setting a maximum heart rate.

A default maximum heart rate is determined by the MIDlet 35 on the basis of the user's entered age. Referring to FIG. 6, the default maximum heart rate is calculated (step s11) according to Equation 1:

$$\text{maximum heart rate}=208-(0.7\times\text{age}) \quad (1)$$

where age is the user's age entered by the user in years.

Figure 7:
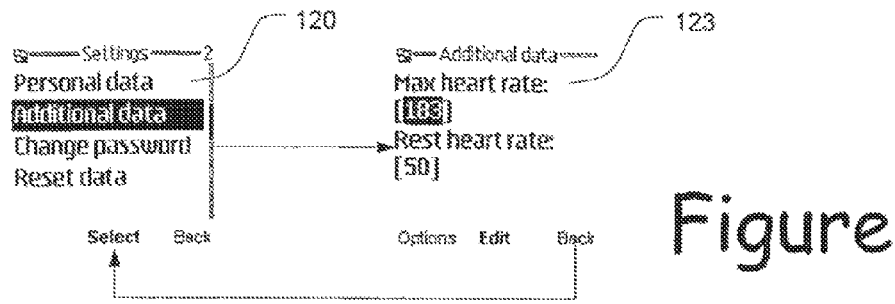
FIG. 7 illustrates the user interface of the MIDlet 35 for additional data entry.

Referring to FIG. 7, if the user selects the Additional Data option from the settings list screen 120, the user is presented with heart rate edit screen 123. The heart rate edit screen 123 includes two textfield elements which enable the user to enter their maximum and resting heart rates respectively. If the user has not previously entered heart rates, the textfields contain the default values whose determination is described above. If the either of the values is changed by the user, the new value is written to the record store. The user can return to the settings list screen 120 by selecting the Back command.

Figure 8:
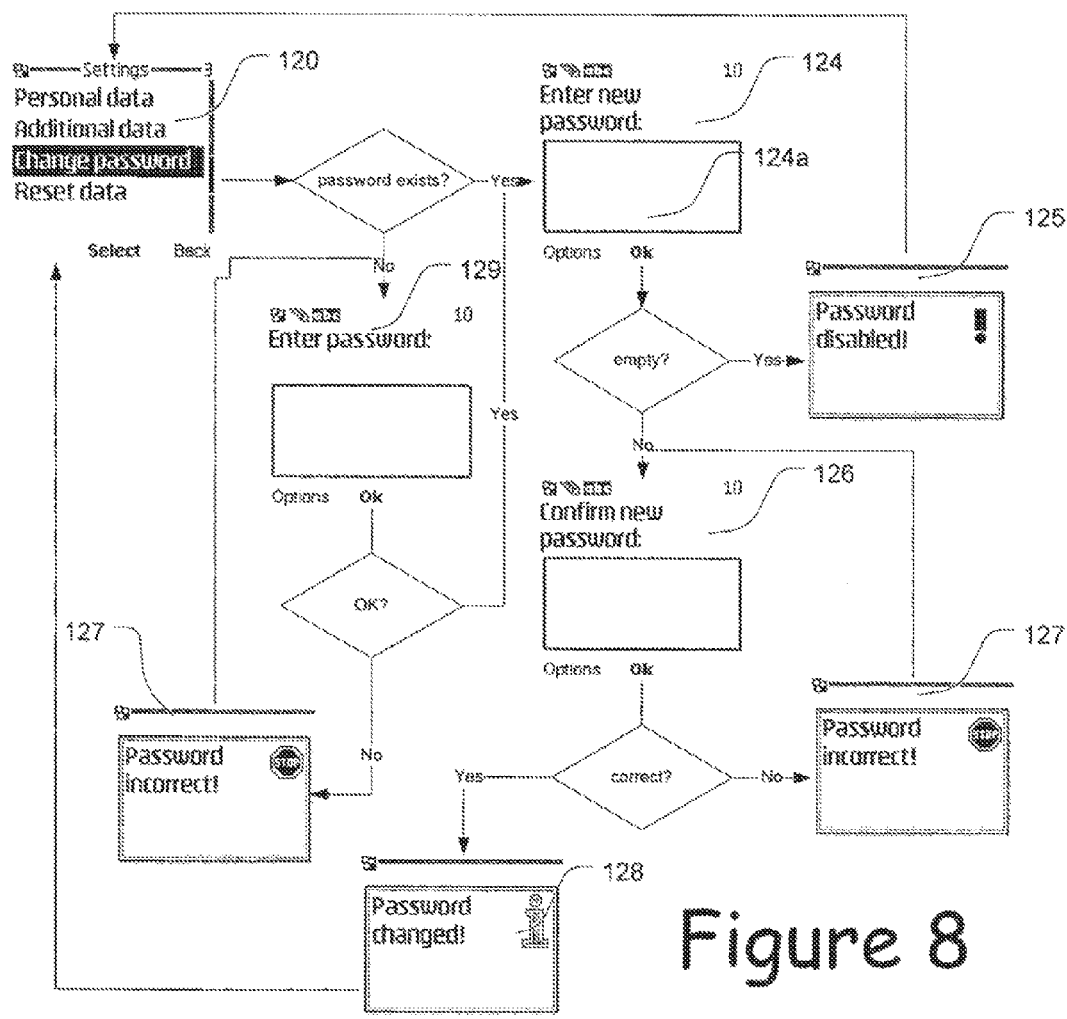
FIG. 8 illustrates the user interface of the MIDlet 35 for password setting.

Referring to FIG. 8, if the user selects the Change Password option from the settings list screen 120, it is determined whether a password has been previously entered. If a password has not been set previously, the user is presented with an enter new password screen 124. When the user has selected the OK command of the new password screen 124, it is determined whether the text property of the new password textfield 124a is an empty string. If the text property of the new password textfield 124a is an empty string, a password disabled screen 125 is displayed for a short period and the MIDlet 35 displays the settings list screen 120 again.

If, however, the text property of the new password textfield 124a is not an empty string, the user is presented with a confirm password screen 126. The user must correctly enter their new password at this point. If their new password is not correctly entered, a password incorrect screen 127 is displayed for a short period before the password entry screen 126 is displayed again. However, if the password is correctly re-entered, a password changed screen 128 is displayed for a short period and the MIDlet 35 then redisplays the settings list screen 120.

If, after selection of Change Password option, it is determined that a password has already been set, the user is presented with a password entry screen 129. If the user incorrectly enters their password into the password entry screen 129, the password incorrect screen 127 is displayed for a short period after which the password entry screen 129 is redisplayed. If, however, the user enters their password correctly, the enter new password screen 124 is displayed and the user can set up the new password as described above.

Figure 9:
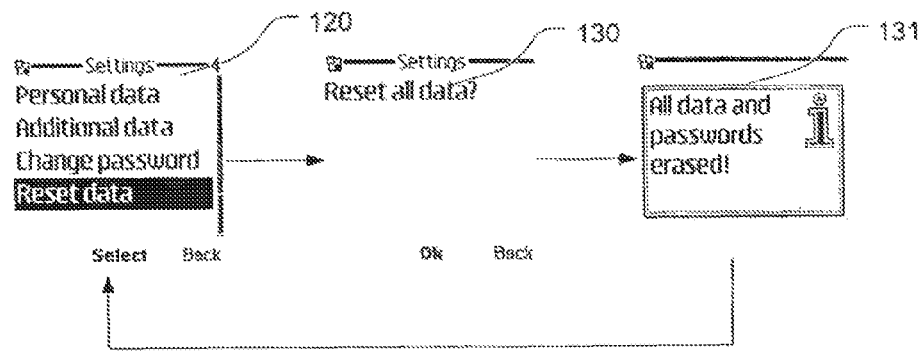
FIG. 9 illustrates the user interface of the MIDlet 35 for clearing user settings.

Referring to FIG. 9, if the user selects the Reset data option from the settings list screen 120, a reset confirmation screen 130 is displayed so that the user can confirm that resetting is desired or abort the resetting. If the user confirms that resetting is desired, the user data, including the password, is cleared and a confirmation screen 131 is displayed for a short period. While the confirmation screen is being displayed, the record store is updated.

If, when the MIDlet 35 is instantiated, a valid set of configuration data is successfully read from the record store, the MIDlet 35 is ready for use.

If the user selects the Fast Start option from the main screen, the MIDlet 35 performs a process 133 to guide the user through an independent exercise session 133 which is appropriate for the user.

After the selection of the Fast Start option, the user is presented with an exercise type list screen 140 comprising Fitness Center, Outdoor and Swimming options.

Figure 11:
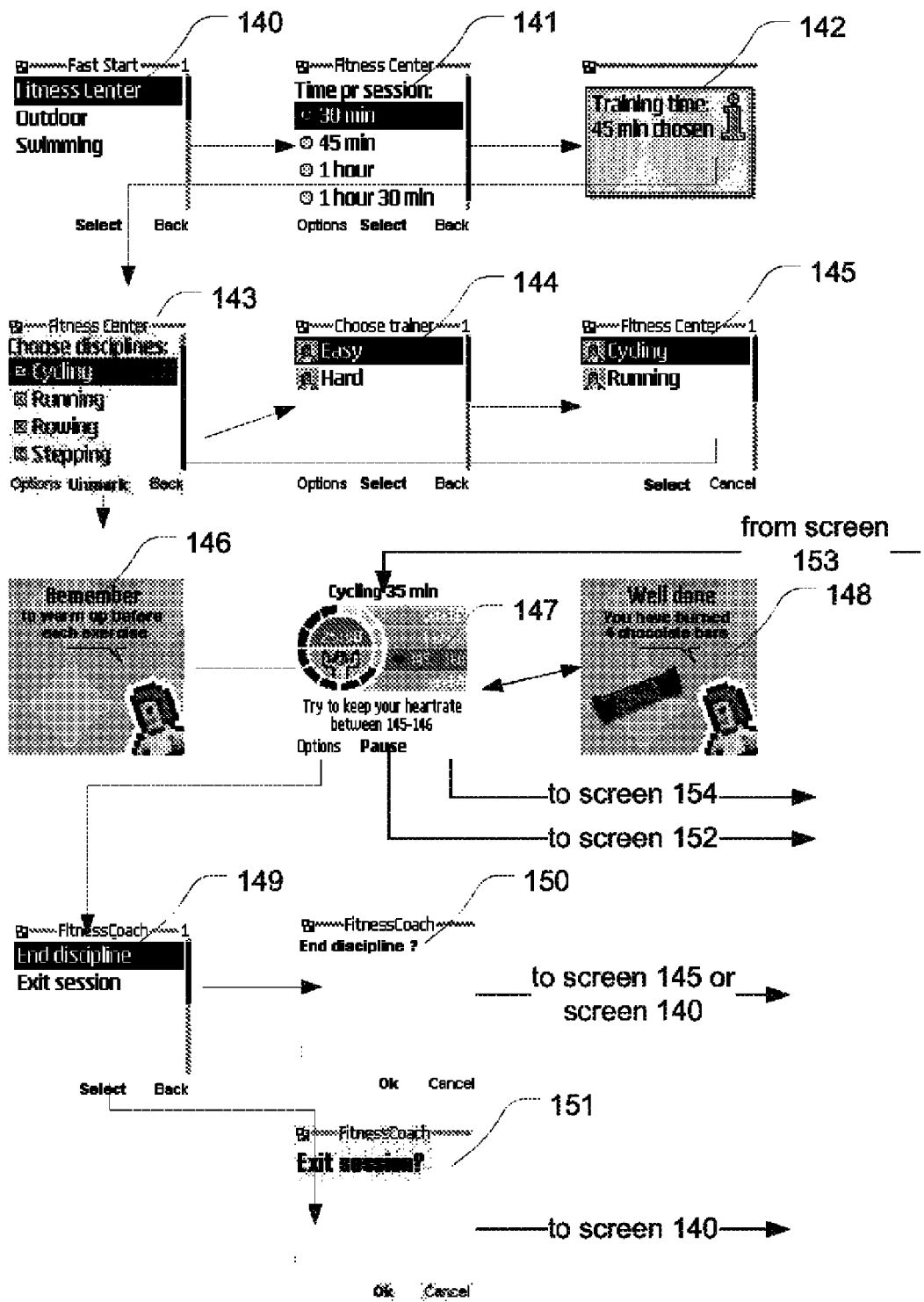
FIG. 11 illustrates the user interface of the MIDlet 35 for an independent exercise session.
Figure 11:
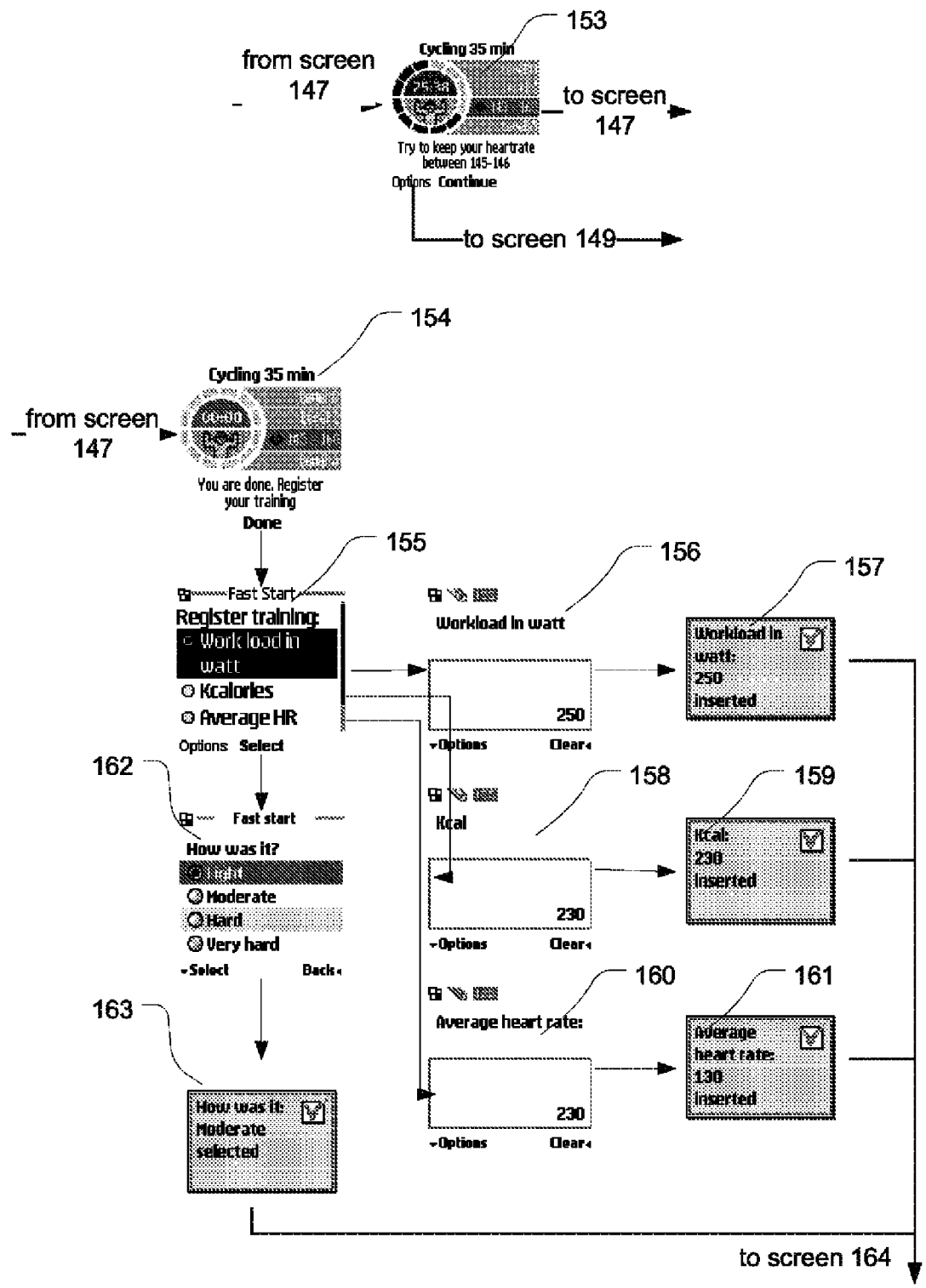
Figure 11:
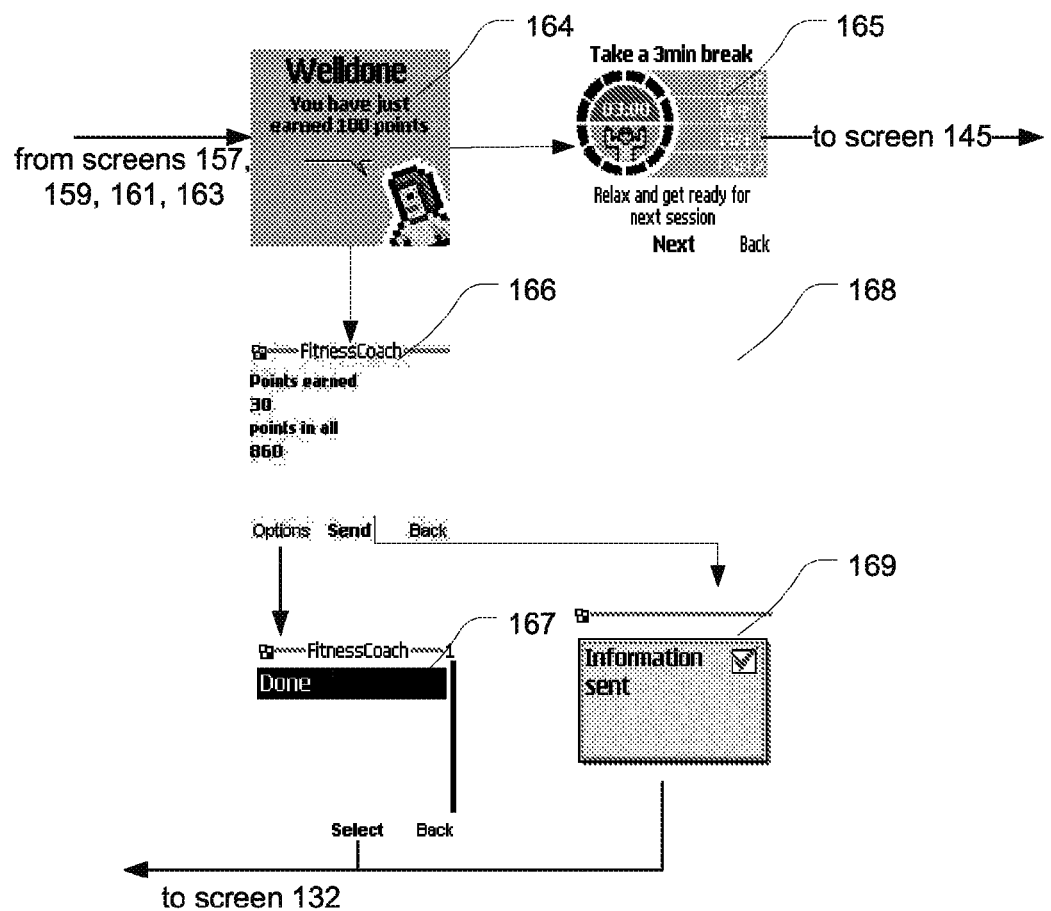

Referring to FIG. 11, if the user selects the Fitness Center option, the user is presented with a session duration list screen 141 which enables the user to select 30, 45, 60 or 90 minutes for the duration of the exercise session. When the user has selected a session duration, the selected duration is displayed for a short period in a session duration confirmation screen 142. The session duration screen 142 is replaced by a discipline selection multiselect list screen 143. The discipline selection multiselect list screen 143 comprises a list of disciplines that are typically available in a fitness center and, in the present example, comprise Cycling, Running, Rowing and Stepping. The user can select one or more of the listed disciplines.

After selecting one or more disciplines, the user is presented with a trainer selection list screen 144 which enables the user to select between hard and easy virtual trainers.

Once the trainer has been selected, the user is presented with a discipline list screen 145 which consists of the selected activities. The user can now select the first discipline to be performed. In the present example, the user has selected the cycling and running disciplines and chooses to do the cycling first. If the user has selected only one discipline, screen 145 is skipped. Icons beside the elements in the discipline list screen 145 indicate whether the disciplines have not been started, been completed or been interrupted.

If the easy trainer has been selected, the activities to be performed in each discipline are selected randomly from the a, b and c sections of Table 8 below for low, moderate and high endurance users respectively. However, if the hard trainer has been selected, the activities to be performed in each discipline are selected randomly from the b, c and d sections of Table 8 below for low, moderate and high endurance users respectively. If a plurality of disciplines has been selected, the activities are selected so as to tend to divide the session duration evenly between the disciplines. It is not essential that either a perfectly even distribution or an exact match to the selected session duration be achieved.

On selecting the starting discipline, the user is presented for a short period with an information screen 146 which reminds the user to warm up before exercising. The information screen 146 is replaced by a exercise guidance screen 147.

Figure 12:
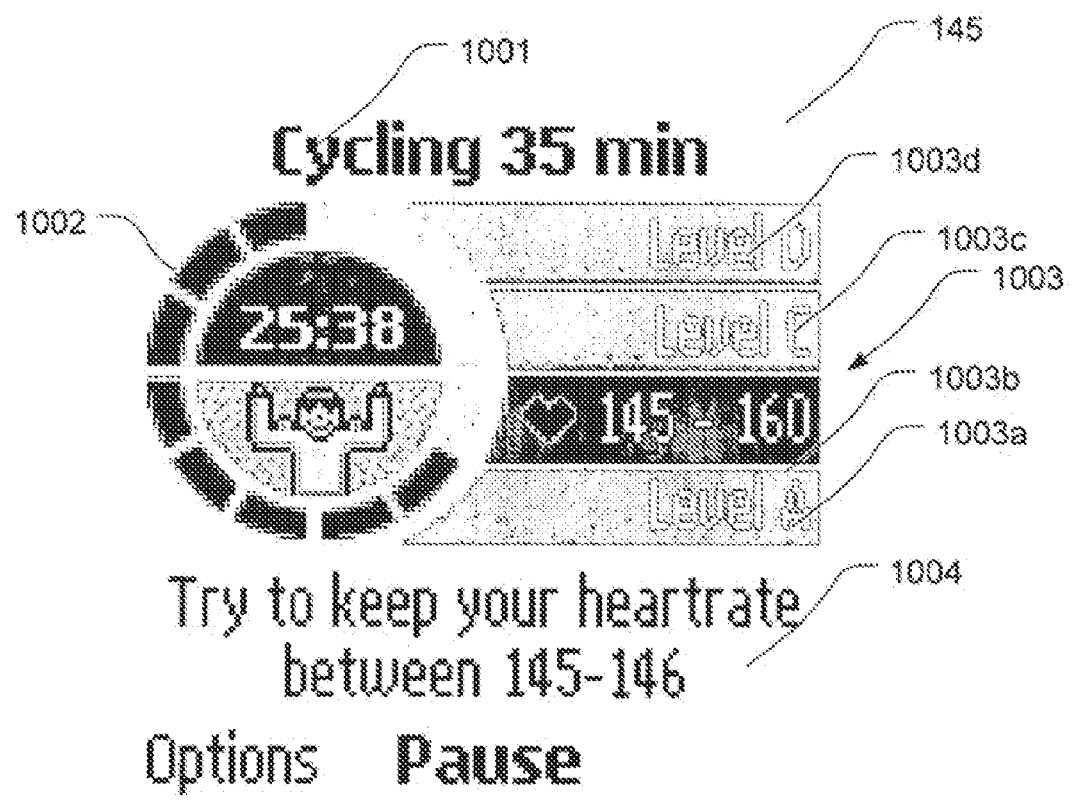
FIG. 12 shows an exercise guidance screen of the MIDlet's user interface.

Referring to FIG. 12, the exercise guidance screen 147 comprises a title 1001, a timer section 1002, an intensity indicator 1003 and an instruction 1004. The title 1001 states the discipline and the duration of the activity. The timer section 1002 comprises a circular graphic with sections that are sequentially lightened to indicate the passage of time. The intensity indicator 1003 comprises four sections 1003a, 1003b, 1003c, 1003d corresponding to respectively to intensity levels a, b, c and d. The section 1003b corresponding current intensity indicates a heart rate target range commensurate with the current intensity. The other section 1003a, 1003c and 1003d merely state the corresponding intensity level. The intensity level is based on the users personal data and additional data, if any. The instruction 1004 may informs the user of a narrower target heart rate within the range corresponding to the current intensity level or that they must change speed, stop or restart when a beep is sounded.

The target heart rate is calculated from the user's personal and additional data.

When the user selects the Start command (not shown) from the exercise guidance screen 147, the MIDlet 35 begins timing the user's performance of the selected discipline. During this period, the MIDlet 35 occasionally displays motivational messages in motivational message screens 148. For instance, a motivational message may inform a user of a foodstuff that has a calorific value corresponding to the amount of energy notionally produced by the user while performing the discipline. The motivational message screens 148 are displayed for short periods before the display reverts to the exercise guidance screen 147.

If the user selects the Options from the exercise guidance screen 147, the user is presented with an options menu 149 comprising End discipline and Exit session options. If the user selects the End discipline option, the user is presented with an end discipline confirmation screen 150 and, if the user confirms that the discipline is to be ended, the MIDlet 35 stops timing and displays the discipline list screen 145 again, if more than one discipline was selected and at least one has not been attempted, otherwise the exercise type list screen 140 is displayed again.

If the user selects the Exit session option, the user is presented with an exit session confirmation screen 151 and, if the user confirms that the discipline is to be ended, the MIDlet 35 stops timing and displays the exercise type list screen 140 again.

If the user selects the Pause command from the exercise guidance screen 147, the user is presented with a pause confirmation screen 152. If the user confirms that the current discipline is to be paused, a paused discipline screen 153 is displayed. The paused discipline screen 153 is the exercise guidance screen 147 with the area 1002a bearing the time colored red and the time flashing, and the Pause command replaced with a Continue command. The MIDlet's timing of the discipline is paused while the paused discipline screen 153 is being displayed. When the user selects the Continue command from the paused discipline screen 153, the MIDlet 35 restarts its timing operation and displays the exercise guidance screen 147 again. The user can also end the current discipline or exit the current session by selecting Options from the paused discipline screen 153 which takes the user to the options menu 149.

When the period set for the current discipline has elapsed, allowing for any pauses, the MIDlet 35 displays a discipline completed screen 154. The MIDlet 35 also produces an audible indication that the set period has elapsed. When the user acknowledges the ending of the discipline by selecting the Done command of the discipline completed screen 154, a registration list screen 155 is displayed.

The registration list screen 155 lists different options for registering the completed discipline. The options comprise Work load in Watts, kcalories, average HR and How was it? (Hidden in FIG. 11 but can be scrolled down to). The first three options require the user to have access to suitable measuring devices. These may be standalone devices or devices integrated into exercise apparatuses. The fourth option enables a user to provide feedback in the absence of suitable measuring devices.

If the user selects Work load in Watts, the user is presented with a work load entry screen 156 which enables the user to enter the average power produced during performance of the selected discipline. When the average power has been input, the user is presented with a confirmation screen 157 for a short period.

If the user selects kcalories, the user is presented with a kilocalories entry screen 158 which enables the user to enter the energy used during performance of the selected discipline. When the energy used has been input, the user is presented with a confirmation screen 159 for a short period.

If the user selects Average HR, the user is presented with an average heart rate entry screen 160 which enables the user to enter their average heart rate during performance of the selected discipline. When the user's average heart rate has been input, the user is presented with a confirmation screen 161 for a short period.

If the user selects How was it?, the user is presented with an experienced intensity list screen 162 which enables the user to select a level of intensity corresponding to their experience of the performance of the selected discipline. Help in making the selection can be obtained by selecting Options from the experienced intensity list screen 162. When the user has selected the appropriate intensity, the user is presented with a confirmation screen 163 for a short period.

The MIDlet 35 now calculates a number of points which represent the value of the performance of the selected discipline in arbitrary units. The calculation of the points will be described below.

The points earned is displayed for a short period in a completion message screen 164. Then, if there remain uncompleted disciplines in the current session, a rest information screen 165 is displayed. The user can select a Next command from the rest information screen 165 which returns the user to the discipline list screen 145.

If all disciplines in the current session have been completed, the completion message screen 164 is followed by a points summary screen 166 which displays the points earned in the current session and the total points earned. The points summary screen 166 provides the user with Done and Send commands. Selecting the Done command cause a done confirmation screen 167 to be displayed. If the user confirms that the session should end, the MIDlet 35 displays the main screen 132.

If the user selects the Send command, the MIDlet 35 send a summary of the session to a remote server by SMS. On completion of the transmission, the user is presented with a transmission confirmation screen 169 for a short period after which the main screen 132 is displayed.

Figure 13:
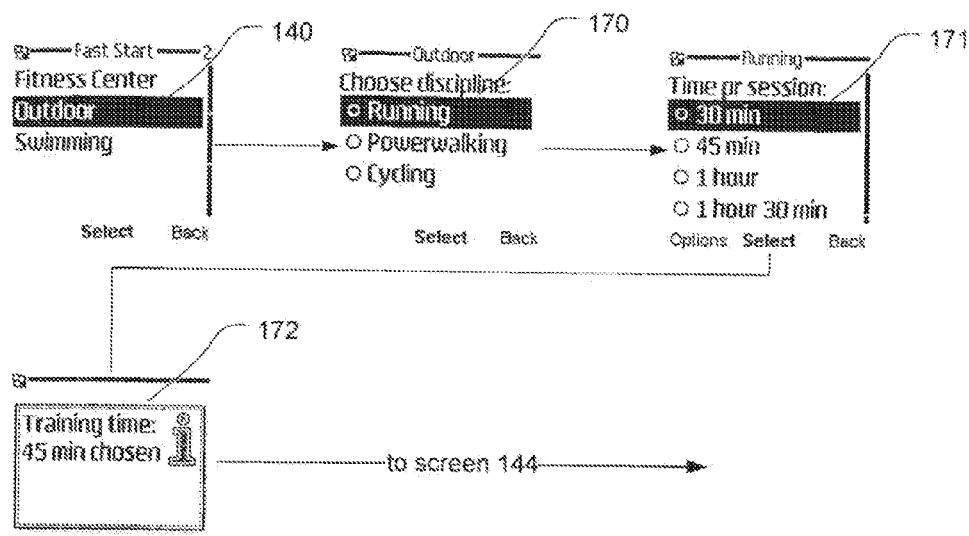
FIG. 13 illustrates further details of the user interface of the MIDlet 35 for an independent exercise session.

Referring to FIG. 13, if the user selects the Outdoor option from the exercise type list screen 140, the user is presented with an outdoor discipline list screen 170. The user is able to select one discipline from the outdoor discipline list screen 170 and on doing so is presented with a session duration screen 171. The session duration screen 171 enables the user to set the duration of the session to 30, 45, 60 or 90 minutes. When the user has selected the desired session duration, a duration confirmation screen 172 is displayed for a short period. After the display of the duration confirmation screen 172, screen 144 is displayed and the session continues as described with reference to FIG. 12.

Figure 14:
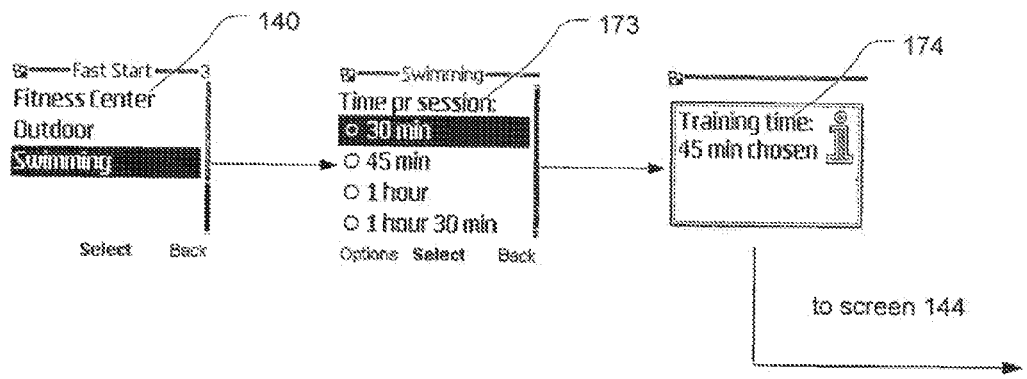
FIG. 14 illustrates still further details of the user interface of the MIDlet 35 for an independent exercise session.

Referring to FIG. 14, if the user selects the Swimming option from the exercise type list screen 140, the user is presented with a session duration screen 173. The session duration screen 173 enables the user to set the duration of the session to 30, 45, 60 or 90 minutes. When the user has selected the desired session duration, a duration confirmation screen 174 is displayed for a short period. After the display of the duration confirmation screen 174, screen 144 is displayed and the session continues as described with reference to FIG. 11.

The calculation of points for a session or discipline by the MIDlet 35 will now be described.

The points are awarded according to the Equation 2:

$$points = t \times intensity \qquad (2)$$

where t is the duration of the exercising in minutes and intensity is a measure of a person's performance relative to a theoretical maximum. The intensity is calculated differently depending on the way in which performance is entered, i.e. the choice made at screen 155 in FIG. 11.

If the performance has been entered in terms of average power, the relative performance is obtained as a percentage from Equation 3:

$$\text{relative performance} = \frac{(\text{actual average power}) \times 100}{\text{theoretical maximum average power}} \quad (3)$$

The theoretical maximum average power is obtained according to Table 1 below.

Table 1

| Weight | Men | | | Women | | |
|---|---|---|---|---|---|---|
| | Low Endurance | Moderate Endurance | High Endurance | Low Endurance | Moderate Endurance | High Endurance |
| 0-59 kg | 210 W | 250 W | 290 W | 170 W | 210 W | 250 W |
| 60-79 kg | 250 W | 275 W | 330 W | 210 W | 230 W | 290 W |
| 80-99 kg | 275 W | 300 W | 375 W | 230 W | 260 W | 330 W |
| 100-300 kg | 300 W | 330 W | 420 W | 260 W | 290 W | 375 W |

Thus, a 55 kg woman having a high endurance and who had generated an average power of 210 W for 30 minutes would have achieved a relative performance of:

$$84\% = \frac{210 \times 100}{250}$$

The relative performance is converted into an intensity value according to Table 2 below.

TABLE 2

| Relative Performance | Intensity |
|---|---|
| 0-39% | 0 |
| 40-64% | 1 |
| 65-74% | 2 |
| 75-84% | 4 |
| 85-95% | 6 |

Thus, in the present example, the intensity is 4, giving 4×30=120 points.

If the performance has been entered in terms of kilocalories, the total energy used in kilocalories is used to obtain an average power value. The average power value is obtained from Table 3 below using the result of:

$$\frac{\text{kilocalories}}{t}$$

where t is the duration of the exercising in minutes.

TABLE 3

| kcal/min | Watts |
|---|---|
| 1.2 | 20 |
| 1.8 | 30 |
| 2.4 | 40 |
| 3.0 | 50 |
| 3.6 | 60 |
| 4.2 | 70 |
| 4.8 | 80 |
| 5.4 | 90 |
| 6.0 | 100 |
| 6.6 | 110 |
| 7.2 | 120 |
| 7.8 | 130 |
| 8.4 | 140 |
| 9.0 | 150 |
| 9.6 | 160 |
| 10.2 | 170 |
| 10.9 | 180 |
| 11.5 | 190 |
| 12.1 | 200 |
| 12.7 | 210 |
| 13.3 | 220 |
| 13.9 | 230 |
| 14.5 | 240 |
| 15.1 | 250 |
| 15.7 | 260 |
| 16.3 | 270 |
| 16.9 | 280 |
| 17.5 | 290 |
| 18.1 | 300 |
| 18.7 | 310 |
| 19.3 | 320 |
| 19.9 | 330 |
| 20.5 | 340 |
| 21.1 | 350 |
| 21.7 | 360 |
| 22.3 | 370 |
| 22.9 | 380 |
| 23.5 | 390 |
| 24.2 | 400 |
| 24.7 | 410 |
| 25.3 | 420 |
| 25.9 | 430 |
| 26.5 | 440 |
| 27.1 | 450 |
| 27.7 | 460 |
| 28.3 | 470 |
| 28.9 | 480 |
| 29.5 | 490 |
| 30.1 | 500 |
| 30.7 | 510 |

Thus, if the woman in the example above had generated 300 kilocalories in 30 minutes, the equivalent average power would have been 170 W (10.2 kcal being the nearest value to 10 kcal in Table 3).

170 W would give a relative performance of:

$$68\% = \frac{170 \times 100}{250}$$

from Equation 3 and, from Table 2 and Equation 2, 60 points.

If the performance has been entered in terms of average heart rate (HR), the points are based on the relative resistance (RR) obtained from the Karvonen formula:

$$RR = \frac{\text{average work } HR - \text{rest } HR}{\max HR - \text{rest } HR} \times 100 \quad (4)$$

Thus, for a person having a resting heart rate of 50 bpm and a maximum heart rate of 181 bpm, an average work heart rate during exercise of 140 bpm would give a relative performance of 69%. The intensity can then be obtained in accordance with Table 4 below.

TABLE 4

| Relative Performance | Intensity |
|---|---|
| 0-50% | 0 |
| 50-64% | 1 |
| 65-74% | 2 |
| 75-84% | 4 |
| 85-95% | 6 |

In this example, the intensity is 2, giving 60 points for 30 minutes of exercise.

If the performance has been entered using the How was it? options, the intensity is obtained from a direct mapping from the selected option to intensity as set out in Table 5 below.

TABLE 5

| How was it? | Intensity |
|---|---|
| Easy | 1 |
| Moderate | 2 |
| Hard | 4 |
| Very Hard | 6 |

The MIDlet 35 includes code to achieve the same result as the calculations described above for calculating points.

Referring back to FIG. 10, if the user selects the Planner option, the MIDlet 35 enters a process 134 for guiding the user through the creation of an exercise program appropriate for the user.

Figure 15:
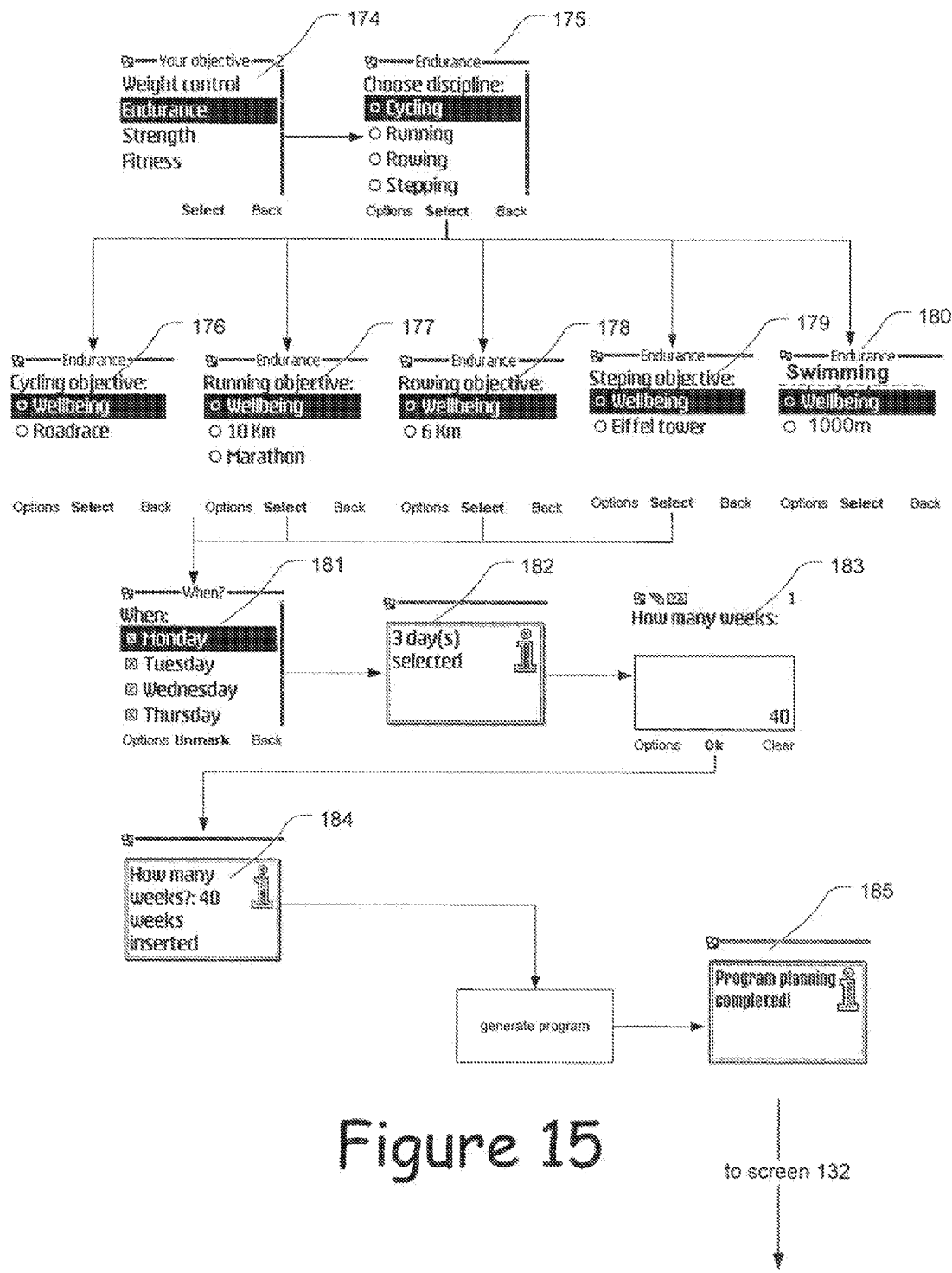
FIG. 15 illustrates the user interface of the MIDlet 35 for planning an endurance exercise program.

Referring to FIG. 15, when the user selects the Planner option, the user is presented with a program type list screen 174 from which the user can select weight control, endurance, strength and fitness programs. The weight control and fitness programs combine endurance and strength disciplines in different ratios.

The weight control option is not displayed to high endurance users and cannot therefore be selected by them.

If the user selections the Endurance option, the user is presented with a discipline selection list screen 175 is displayed so that the user can select the discipline that they wish to perform during their new program. In the present example, the options available are Cycling, Running, Rowing, Stepping and Swimming.

If the user selects Cycling, a cycling objective list screen 176 is displayed. The user can choose between Wellbeing and Roadrace as their objective. Roadrace is a more ambitious objective than Wellbeing.

If the user selects Running, a running objective list screen 177 is displayed. The running objective list screen 177 enables the user to choose between, at most, Wellbeing, 10 km and Marathon.

If the user selects Rowing, a rowing objective list screen 178 is displayed. The rowing objective list screen 178 enables the user to choose between Wellbeing and 6 km.

If the user selects Stepping, a running objective list screen 179 is displayed. The stepping objective list screen 179 enables the user to choose between Wellbeing and Eiffel tower.

If the user selects Swimming, a running objective list screen 180 is displayed. The swimming objective list screen 180 enables the user to choose between Wellbeing and 1000 m.

When the user has selected their objective, a weekday multiselect list screen 181. The user can select the days on which the user wishes to exercise. There are limitations on the number of days that can be selected. A user who has low endurance cannot select six or seven days. Additionally, if the objective is a marathon, at least three days must be selected.

When the user has selected a valid set of days, a selected days confirmation screen 182 is displayed for a short period.

Next, the user is presented with a weeks entry screen 183 which enables the user to enter the number of weeks that the program is to run for. The entered number of weeks must be in the range 5 to 50. There are limitations on the minimum number of weeks which are set out in Table 6 below.

TABLE 6

| Discipline | Objective | Low End. | Mod. End. | High End. |
|---|---|---|---|---|
| Running | Wellbeing | 5 | 5 | 5 |
|  | 10 km | 10 | 5 | 5 |
|  | Marathon | 20 | 15 | 10 |
| Cycling | Wellbeing | 5 | 5 | 5 |
|  | Roadrace | 20 | 15 | 10 |
| Rowing | Wellbeing | 5 | 5 | 5 |
|  | 6 km | 10 | 5 | 5 |
| Swimming | Wellbeing | 5 | 5 | 5 |
|  | 1000 m | 10 | 5 | 5 |
| Stepping | Wellbeing | 5 | 5 | 5 |
|  | Eiffel tower | 10 | 5 | 5 |

The entered number of weeks is confirmed in a weeks confirmation screen 184 which is displayed for a short period.

After the number of weeks has been confirmed, the MIDlet 35 generates the exercise program and stores it in its record store and then displays planning complete screen 185 for a short period.

Figures 16, 17:
FIG. 16 is a flowchart illustrating generation of an endurance
FIG. 17 illustrates the distribution of activity classes across the sessions of an exercise program.

Referring to FIG. 16, the exercise program generation starts with the determination of the distributions of sessions of different intensities (step s21).

The exercise sessions are classified in increasing intensity into four classes a, b, c and d. The distribution of the four classes among the sessions is obtained in accordance with Table 7 below, in dependence on the selected objective option, the number exercise sessions per week and the endurance of the user. The Wellbeing objectives are Grade 1 objectives. The 10 km, 6 km, 1000 m and Eiffel tower objectives are Grade 2 objectives and the Roadrace and Marathon objectives are Grade 3 objectives.

TABLE 7

| | | Sessions per Week | | | | | | | | | | | | | | | |
|---|---|---|---|---|---|---|---|---|---|---|---|---|---|---|---|---|---|
| | | 2 | | | 3 | | | 4 | | | 5 | | | 6 | | | 7 | | |
| int. | end. | L | M | H | L | M | H | L | M | H | L | M | H | L | M | H | L | M | H |
| Grade 1 | | | | | | | | | | | | | | | | | | | |
| a | | 30 | 10 | 0 | 30 | 13 | 0 | 40 | 33 | 25 | 40 | 31 | 20 | 45 | 38 | 30 | 50 | 43 | 35 |
| b | | 35 | 45 | 50 | 35 | 49 | 60 | 30 | 32 | 35 | 30 | 35 | 40 | 25 | 32 | 40 | 25 | 32 | 40 |

TABLE 7-continued

Sessions per Week

| | | 2 | | | 3 | | | 4 | | | 5 | | | 6 | | | 7 | | |
|---|---|---|---|---|---|---|---|---|---|---|---|---|---|---|---|---|---|---|---|
| int. | end. | L | M | H | L | M | H | L | M | H | L | M | H | L | M | H | L | M | H |
| | c | 25 | 25 | 25 | 25 | 22 | 20 | 20 | 20 | 20 | 30 | 25 | 20 | 20 | 18 | 15 | 20 | 15 | 10 |
| | d | 10 | 20 | 25 | 10 | 16 | 20 | 10 | 15 | 20 | 0 | 9 | 20 | 10 | 12 | 15 | 5 | 10 | 15 |
| | | 100 | 100 | 100 | 100 | 100 | 100 | 100 | 100 | 100 | 100 | 100 | 100 | 100 | 100 | 100 | 100 | 100 | 100 |
| Grade 2 | | | | | | | | | | | | | | | | | | | |
| | a | 25 | 8 | 0 | 30 | 13 | 0 | 30 | 25 | 20 | 40 | 35 | 30 | 45 | 38 | 30 | 50 | 43 | 35 |
| | b | 25 | 8 | 0 | 25 | 17 | 10 | 30 | 30 | 30 | 30 | 30 | 30 | 25 | 32 | 40 | 25 | 32 | 40 |
| | c | 25 | 42 | 50 | 25 | 39 | 50 | 25 | 25 | 25 | 25 | 23 | 20 | 20 | 18 | 15 | 20 | 15 | 10 |
| | d | 25 | 42 | 50 | 0 | 31 | 40 | 15 | 20 | 25 | 5 | 12 | 20 | 10 | 12 | 15 | 5 | 10 | 15 |
| | | 100 | 100 | 100 | 100 | 100 | 100 | 100 | 100 | 100 | 100 | 100 | 100 | 100 | 100 | 100 | 100 | 100 | 100 |
| Grade 3 | | | | | | | | | | | | | | | | | | | |
| | a | — | — | — | 40 | 18 | 0 | 40 | 33 | 25 | 45 | 36 | 25 | 50 | 41 | 30 | 50 | 41 | 30 |
| | b | — | — | — | 30 | 47 | 60 | 30 | 32 | 35 | 35 | 37 | 40 | 35 | 37 | 40 | 40 | 42 | 45 |
| | c | — | — | — | 20 | 20 | 20 | 20 | 20 | 20 | 15 | 17 | 20 | 10 | 12 | 15 | 10 | 12 | 15 |
| | d | — | — | — | 10 | 16 | 20 | 10 | 15 | 20 | 5 | 10 | 15 | 5 | 10 | 15 | 0 | 5 | 10 |
| | | — | — | — | 100 | 100 | 100 | 100 | 100 | 100 | 100 | 100 | 100 | 100 | 100 | 100 | 100 | 100 | 100 |

By way of example, if a moderate endurance user chooses Wellbeing and four sessions per week, the program would contain 25% class a sessions, 30% class b session, 25% class c sessions and 20% class d sessions.

Once the session class distribution has been determined, it is necessary to create a varied distribution of activities, meeting the determined class distribution criterion, across all but the last week of the program (step s22). Thus, if, for example, the user has specified a 15 week program, the activity distribution process distributes activities across, in this example, 4 sessions in each of 14 weeks, giving a total of 56 sessions. Of these sessions, 14 will be class a sessions, 17 will be class b sessions, 14 will be class c sessions and 11 will be class d sessions. The numbers of sessions of each class are rounded as necessary.

The activities are allocated to sessions in the order class d to class a. A class d step value is initially obtained by integer dividing the number of sessions by the number of class a sessions, i.e. 56 div 11=5 in the present example. Class d activities are therefore allocated to sessions 5, 10, 15, 20. 25, 30, 35, 40, 45, 50 and 55. The actual activities are chosen at random from the class d entries, i.e. activities d1, . . . , d8, in Table 8 below. The process is then repeated for class c sessions. In the present example, the class c step value is 56 div 14=4. The class c sessions would therefore be 4, 8, 12, 16, 21 (session 20 is already occupied by a class d activity), 24, 28, 32, 36, 41 (session 40 is already occupied by a class d activity), 44, 48, 52 and 56. For the class b sessions, the step value is 56 div 17=3 and the class b sessions are 3, 6, 9, 13 (session 12 is already occupied by a class c activity), 17 (session 15 is already occupied by a class d activity and session 16 is already occupied by a class c activity), 18, 22 (session 21 is already occupied by a class c activity), 26 (session 24 is already occupied by a class c activity and session 25 is already occupied by a class d activity), 27, 31 (session 30 is already occupied by a class d activity), 33, 37 (session 36 is already occupied by a class c activity), 39, 42, 46 (session 45 is already occupied by a class d activity), 49 (session 48 is already occupied by a class c activity) and 51. Finally, the remaining sessions are made class a sessions. The final session pattern is shown in FIG. 17.

TABLE 8

| Class and Type | | Warm up | Intervals | Duration | Pause | Warm Down | Total time |
|---|---|---|---|---|---|---|---|
| a | 1 | C | 5 | | 15 | | 5 | 25 |
| | 2 | C | 5 | | 20 | | 5 | 30 |
| | 3 | C | 5 | | 25 | | 5 | 35 |
| | 4 | C | 5 | | 30 | | 5 | 40 |
| | 5 | C | 5 | | 40 | | 5 | 50 |
| b | 1 | C | 5 | | 20 | | 5 | 30 |
| | 2 | C | 5 | | 25 | | 5 | 35 |
| | 3 | C | 5 | | 30 | | 5 | 40 |
| | 4 | F | 5 | | 20 | | 5 | 30 |
| | 5 | F | 5 | | 25 | | 5 | 35 |
| c | 1 | C | 5 | | 20 | | 3 | 28 |
| | 2 | C | 5 | | 20 | | 3 | 28 |
| | 3 | C | 5 | | 25 | | 3 | 33 |
| | 4 | F | 5 | | 25 | | 3 | 33 |
| | 5 | C | 5 | | 40 | | 3 | 48 |
| | 6 | I | 5 | 3 | 6 | 3 | 3 | 32 |
| | 7 | I | 5 | 3 | 5 | 3 | 3 | 29 |
| | 8 | I | 5 | 3 | 4 | 2 | 3 | 24 |
| d | 1 | F | 5 | | 20 | | 3 | 28 |
| | 2 | F | 5 | | 20 | | 3 | 28 |
| | 3 | I | 5 | 3 | 6 | 3 | 3 | 32 |
| | 4 | I | 5 | 3 | 5 | 3 | 3 | 29 |
| | 5 | I | 5 | 3 | 4 | 2 | 3 | 24 |
| | 6 | I | 5 | 4 | 3 | 2 | 3 | 26 |
| | 7 | I | 5 | 5 | 2 | 1 | 3 | 22 |
| | 8 | I | 5 | 2 | 10 | 5 | 3 | 33 |

C = continuous, F = fartlek, I = interval

When the sessions of all but the last week have been allocated activities, activities are allocated to the sessions of the final week of the program (step s23). The session classes for the final week are allocated according to Table 9 with the activities selected randomly from Table 8 according to session class.

TABLE 9

| Sessions per week set by user | Monday | Thursday | Friday |
|---|---|---|---|
| 2 | | a | |
| 3 | a | a | |
| 4 | a | a | a |

TABLE 9-continued

| Sessions per week set by user | Monday | Thursday | Friday |
|---|---|---|---|
| 5 |   | a | a |
| 6 | a | d | a |
| 7 | a | d | a |

Thus, in the example given above, the final week consists of two class a sessions on the Thursday and the Friday (see FIG. 17).

The completed program is stored in the MIDlet's record store.

Figure 18:
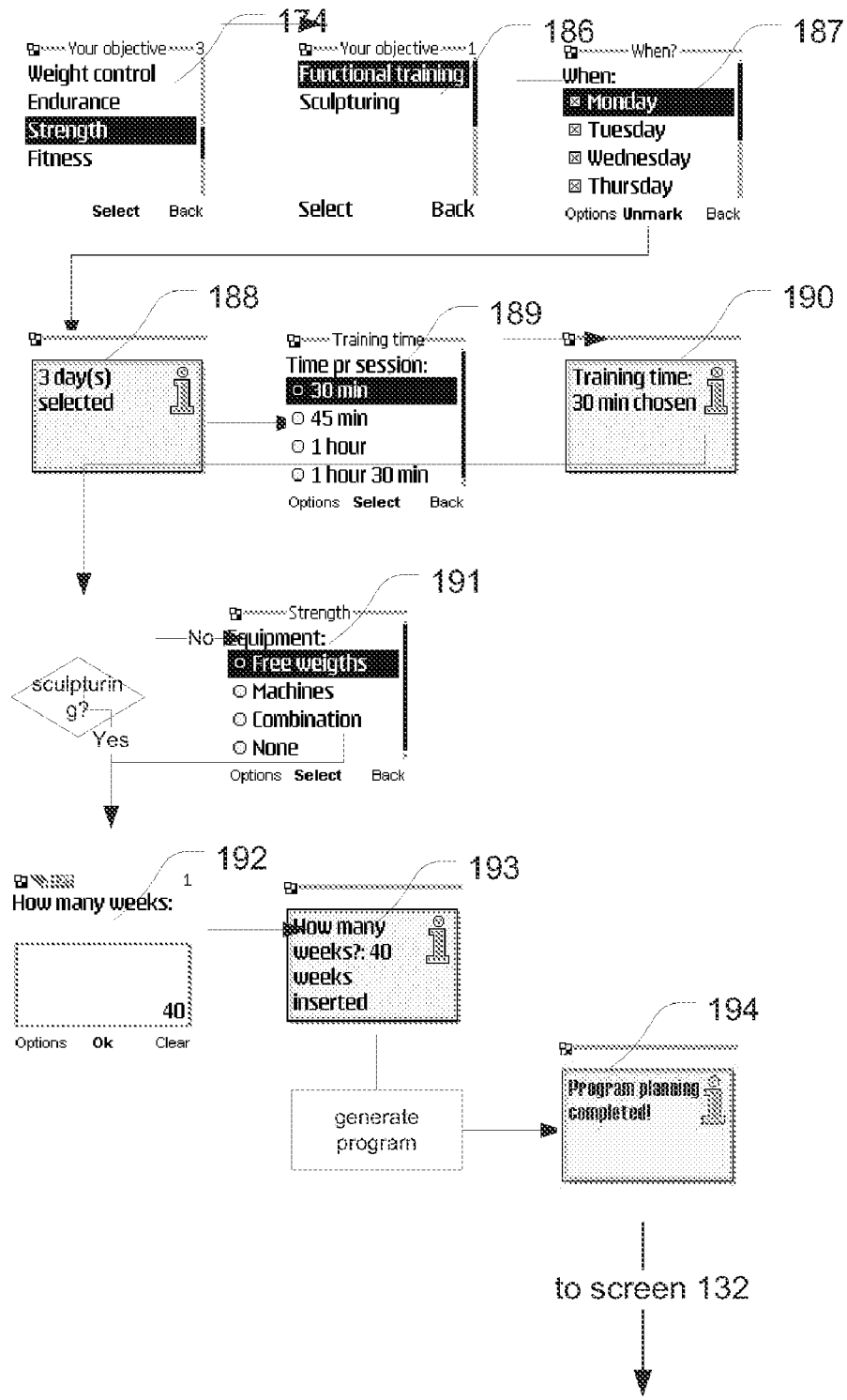
FIG. 18 illustrates the user interface of the MIDlet 35 for planning a strength exercise program.

Referring to FIG. 18, if the user selections the Strength option from the program type list screen 174, the user is presented with an exercise type screen 186 giving the user the opportunity of selecting either Sculpturing or Functional training. However, Functional training is not available to users having low strength. After selecting the exercise type, the user is presented with a weekday multiselect list screen 187. The user can select the days on which the user wishes to exercise. When the user has selected a valid set of days, a selected days confirmation screen 188 is displayed for a short period.

The user is then presented with a session length list screen 189 from which the user can select 30, 45, 60 or 90 minutes as the length for each sessions. The session length selected by the user is confirmed by a session length confirmation screen 190 which displayed for a short period.

If the user has selected Sculpturing from the exercise type screen 186, the user is now presented with an equipment selection list screen 191 which enables to user to specify the equipment, if any, that the user wishes to use. Once the equipment has been specified by the user, Next, the user is presented with a weeks entry screen 192 which enables the user to enter the number of weeks that the program is to last for. The entered number of weeks must be in the range 5 to 50. The entered number of weeks is confirmed in a weeks confirmation screen 193 which is displayed for a short period.

If the user has selected Functional training from the exercise type screen 186, the session length confirmation screen 190 is followed directly by the weeks entry screen 192. Functional training always makes use of free weights.

After the number of weeks that the program is to be last has been entered, the MIDlet 35 generates the exercise program and then displays planning complete screen 194 for a short period.

Figure 19:
FIG. 19 is a flowchart illustrating generation of a strength exercise program.

Referring to FIG. 19, the first step of generating a strength exercise program is to select the program category (step s31) on the basis of the user's strength level, the selected number of sessions per week and the specified session length in accordance with Table 10 below.

TABLE 10

| Strength | Sessions per Week | Session Length (mins) | | | |
|---|---|---|---|---|---|
| Sculpturing (s) | | | | | |
| | | 30 | 45 | 60 | 90 |
| Low | 2 | 1 | 2 | 3 | 4 |
| | 3 | 1 | 2 | 3, 7,11 | 8.12 |
| | 2 | 1 | 2 | 3 | 4 |
| Moderate | 2 | 1 | 2 | 3, 4 | |
| | 3 | 1 | 2 | 3, 7, 11 | 8.12 |
| | 4 | 5, 9 | 6 | 7, 11 | — |

TABLE 10-continued

| Strength | Sessions per Week | Session Length (mins) | | | |
|---|---|---|---|---|---|
| High | 2 | 1 | 2 | 3 | 4 |
| | 3 | 1 | 2 | 3, 7, 11 | 8, 12 |
| | 4 | 5, 9 | 6 | 7, 11 | 8, 12 |
| | 5 | 20 | 21 | 22 | — |
| | 6 | 20 | 21 | 22 | — |
| Functional (f) | | | | | |
| High | 2 | 1 | 13 | 14 | 15 |
| | 3 | 1 | 13 | 14 | 15 |
| | 4 | 16 | 17 | 18 | 19 |

By way of example, if a moderately strong user selects three one-hour sessions per week of sculpturing, the program category is selected at random from categories 3, 7 and 11. In many cases, there is only one program category available and in these cases the available category must be selected.

Once the program category has been obtained, the exercise combinations available for the selected category are obtained in accordance with Table 11 below (step s32).

TABLE 11

| Category | Exercise Combinations | Sets |
|---|---|---|
| 1 | chest 1, back 1, legs 1, abs 1, lower back 1 | 3 sets |
| 2 | 1 + shoulders 1, triceps 1 or biceps 1 | 3 sets |
| 3 | 1 + shoulders 1, triceps 1, biceps 1, legs 2 | 3 sets |
| 4 | 3 + chest 2 or back 2, | 3 sets |
| 5.1 | chest 1, back 1, shoulders 1, triceps 1, biceps 1 | 3 sets |
| 5.2 | legs 1, legs 2, legs 3, lower back 1, abs 1 | 3 sets |
| 6.1 | 5.1 + chest 2, back 2 | 3 sets |
| 6.2 | 5.2 + legs 4, abs 2 | 3 sets |
| 7.1 | 6.1 + shoulders 2 | 3 sets but 4 sets in chest 1, back 1 |
| 7.2 | 6.2 + abs 3 | 3 sets but 4 sets in legs 1 |
| 8.1 | 7.1 + back 3, biceps 2 or triceps 2 | 3 sets but 4 sets in chest 1, back 1 |
| 8.2 | 7.2 | 3 sets but 4 sets in legs 1, legs 2, legs 3 |
| 9.1 | chest 1, chest 2, shoulders 1, triceps 1, abs 1 | 3 sets |
| 9.2 | legs 1, back 1, back 2, lower back 1, biceps 1 | 3 sets |
| 10.1 | 9.1 + shoulders 2 | 3 sets |
| 10.2 | 9.2 + legs 2 | 3 sets |
| 11.1 | 10.1 + triceps 2 | 3 sets |
| 11.2 | 10.2 + legs 3 | 3 sets |
| 12.1 | 11.1 + chest 3, abs 2 | 3 sets |
| 12.2 | 11.2 + back 3, biceps 2 | 3 sets |
| 13 | 1 + shoulders | 3 sets |
| 14 | 13 + back 2 | 3 sets |
| 15 | 14 + legs 2 | 3 sets |
| 16.1 | chest 1, back 1, back 2, shoulders 1 | 3 sets |
| 16.2 | legs 1, legs 2, legs 3, lower back 1, abs 1 | 3 sets |
| 17.1 | 16.1 + chest 2 | 3 sets |
| 17.2 | 16.2 + abs 2 | 3 sets |
| 18.1 | 17.1 + shoulders 2 | 3 sets |
| 18.2 | 17.2 + abs 3 | 3 sets |
| 19.1 | 18.1 | 3 sets but 4 sets in chest 1, back 1 |
| 19.2 | 18.2 | 3 sets but 4 sets in legs 1, lower back 1 |
| 20.1 | legs 1, legs 2, legs 3, triceps 1, biceps 1 | 3 sets |

TABLE 11-continued

| Category | Exercise Combinations | Sets |
|---|---|---|
| 20.2 | back 1, back 2, lower back 1, abs 1, abs 2 | 3 sets |
| 20.3 | chest 1, chest 2, chest 3, shoulders 1, shoulders 2 | 3 sets |
| 21.1 | 20.1 + triceps 2, biceps 2 | 3 sets |
| 21.2 | 20.2 + back 3, abs 3 | 3 sets |
| 21.3 | 20.3 | 4 sets |
| 22.1 | shoulders 1, shoulders 2, shoulders 3, shoulders 4, abs 1, abs 2, abs 3 | 3 sets |
| 22.2 | back 1, back 2, back 3, back 4, biceps 1, biceps 2 | 4 sets but 3 sets in back 3, back 4 |
| 22.3 | chest 1, chest 2, chest 3, chest 4, triceps 1, triceps 2 | 4 sets but 3 sets in chest 2, chest 3, chest 4 |
| 22.4 | legs 1, legs 2, legs 3, legs 4, legs 5, lower back | 4 sets but 3 sets in legs 3, legs 4, legs 5 |

In the present example, the category needed to be selected from categories 3, 7 and 11. I will be assumed that category 7 was selected by a random selection process. Table 11 includes two category 7 exercise combinations, categories 7.1 and 7.2.

The available exercise combinations are allocated to cyclically to the sessions of the program (step s33). Thus, if there is only one exercise combination, this combination will be used for all sessions. If there are two exercise combinations, the sessions will alternate between them and if there are more than two exercise combinations, these will be repeated in sessions a recurring sequence.

Each component of an exercise combination differ depending on whether the user has selected machine, free weight or a combination of machine and free weight exercises and may have a plurality of variants within these groups. The available variants are set out in Table 12 below.

TABLE 12

| Exercise |
|---|

Free Weights

| | |
|---|---|
| Legs 1 | squat, lunges |
| Legs 2 | leg curl |
| Legs 3 | legs 1 minus the chosen one |
| Chest 1 | bench press, Bench press incline, dumbell press, dumbell press incline, |
| Chest 2 | bench press decline, dumbell press decline + chest 1 minus the chosen one |
| Back 1 | pull down, bent over barbell row, t-bar row, narrow grib pull down, seated row, one arm dumbell row, vertical row, chin ups |
| Back 2 | back 1 minus the chosen one |
| Back 3 | back 1 minus the chosen ones |
| Back 4 | back flies |
| Shoulders 1 | shoulder press, dumbell press, uprigth row |
| Shoulders 2 | lateral raises, front raises, shoulders 1 minus the chosen one |
| Abdominals (abs) 1 | sit ups, crunches |
| Abdominals (abs) 2 | diagonal crunches, rotating torso |
| Abdominals (abs) 3 | hip raises |
| Lower back | hyper-extensions, back extensions |

Machines

| | |
|---|---|
| Legs 1 | lunges Schmidt, leg press, squat Schmidt |
| Legs 2 | leg curl |
| Legs 3 | knee extension, standing calf raises, seated calf raises, legs 1 minus the chosen one |
| Legs 4 | legs 1 minus the chosen ones |
| Legs 5 | knee extension, standing calf raises, seated calf raises minus the chosen ones |

TABLE 12-continued

| Exercise |
|---|

| | |
|---|---|
| Chest 1 | chest press, bench press Schmidt, bench press incline Schmidt |
| Chest 2 | cable cross, pec. dec, chest 1 minus the chosen one |
| Chest 3 | chest 1 minus the chosen one |
| Chest 4 | chest 2 minus the chosen one |
| Back 1 | pull down, narrow grip pull down, seated row, vertical row |
| Back 2 | back 1 minus the chosen one |
| Back 3 | back 1 minus the chosen ones |
| Back 4 | back flies |
| Shoulders 1 | shoulder press, dumbell press, upright row |
| Shoulders 2 | lateral raises, front raises, shoulders 1 minus the chosen one |
| Shoulders 2 | shoulders 2 minus the chosen ones |
| Shoulders 4 | shrugs |
| Triceps 1 | one arm extensions, French press, kick backs, push downs |
| Triceps 2 | triceps 1 minus the chosen ones |
| Biceps 1 | reachers curl, barbell curl, dumbbell curl, ez-curl |
| Biceps 2 | iceps 1 minus the chosen one |
| Abdominals (abs) 1 | sit ups, crunches |
| Abdominals (abs) 2 | diagonal crunches, rotating torso |
| Abdominals (abs) 3 | hip raises |
| Lower back 1 | hyper-extensions, back extensions |

Combination

| | |
|---|---|
| Legs 1 | squat, lunges, leg press, squat Schmidt |
| Legs 2 | Leg curl |
| Legs 3 | knee extension, standing calf raises, seated calf raises, legs 1 minus the chosen one |
| Legs 4 | deadlift +legs 1 minus the chosen ones |
| Legs 5 | step ups, knee extension, standing calf raises, seated calf raises minus the chosen ones |
| Chest 1 | bench press, bench press incline, dumbell press, dumbell press incline, |
| Chest 2 | cable cross, flies, flies incline, pull over, seated chest press |
| Chest 3 | bench press decline, dumbell press decline +chest 1 minus the chosen one |
| Chest 4 | Chest 2 minus the chosen one |
| Back 1 | pull down, bent over barbell row, t-bar row, narrow grib pull down, seated row, one arm dumbell row, vertical row, chin ups |
| Back 2 | back 1 minus the chosen one |
| Back 3 | back 1 minus the chosen ones |
| Back 4 | back flies |
| Shoulders 1 | shoulder press, dumbell press, upright row |
| Shoulders 2 | lateral raises, front raises, shoulders 1 minus the chosen one |
| Shoulders 2 | shoulders 2 minus the chosen ones |
| Shoulders 4 | shrugs |
| Triceps 1 | one arm extensions, French press, kick backs, push downs |
| Triceps 2 | triceps 1 minus the chosen ones |
| Biceps 1 | preachers curl, barbell curl, dumbbell curl, ez-curl |
| Biceps 2 | biceps 1 minus the chosen one |
| Abdominals (abs) 1 | sit ups, crunches |
| Abdominals (abs) 2 | diagonal crunches, rotating torso |
| Abdominals (abs) 3 | hip raises |
| Lower back | hyper-extensions, back extensions |

In the present example, if the user had selected Machines from the equipment selection list screen 193, the 7.1 and 7.2 category exercises would be used. The category 7.1 and 7.2 variants for the user are set out in Table 13 below.

TABLE 13

| Category | Exercise | Variant |
|---|---|---|
| 7.1 | chest 1 | chest press |
| | | bench press Schmidt |
| | | bench press incline Schmidt |
| | back 1 | pull down |
| | | narrow grip pull down |
| | | seated row |
| | | vertical row |
| | shoulders 1 | shoulder press |
| | | dumbell press |
| | | upright row |
| | biceps 1 | preachers curl |
| | | barbell curl |
| | | dumbell curl |
| | | ez-curl |
| | triceps 1 | one arm extensions |
| | | French press |
| | | kick backs |
| | | push downs |
| | chest 2 | cable cross |
| | | pec. dec |
| | | chest press |
| | | bench press Schmidt |
| | | bench press incline Schmidt |
| | back 2 | pull down |
| | | narrow grip pull down |
| | | seated row |
| | | vertical row |
| | shoulders 2 | lateral raises |
| | | front raises |
| | | shoulder press |
| | | dumbell press |
| | | upright row |
| 7.2 | legs 1 | lunges Schmidt |
| | | leg press |
| | | squat Schmidt |
| | legs 2 | leg curl |
| | legs 3 | knee extension |
| | | standing calf raises |
| | | seated calf raises |
| | | lunges Schmidt |
| | | leg press |
| | | squat Schmidt |
| | lower back 1 | hyper-extensions |
| | | back extensions |
| | abs 1 | sit ups |
| | | crunches |
| | legs 4 | lunges Schmidt |
| | | leg press |
| | | squat Schmidt |
| | abs 2 | diagonal crunches |
| | | rotating torso |
| | abs 3 | hip raises |

An array having a column for each session and a row for each exercise in the selected exercise category is now populated with exercise variants (step s34). An initial variant of each exercise of each category is selected. Where the sets of variants of different exercises overlap, the chosen variants must be different. These selected variants are then added to the array in the elements for the appropriate sessions and exercises. If there are 10 or less week's worth of sessions, these exercises are used throughout the program.

If the program is to last for more than ten weeks, three of the exercise variants are replaced with unused variants for the 11$^{th}$ and succeeding weeks. Thereafter, if the program is sufficiently long, further groups of three exercise variants are replaced every five weeks. Only exercise variants in the original selection can be replaced until all of the originally selected exercise variants have been replaced. The replacing variants may not duplicate an exercise variant already in the array.

When the array has been populated, it is saved to the MIDlet's record store and the MIDlet 35 displays a planning complete screen 195 for a short period.

Figure 20:
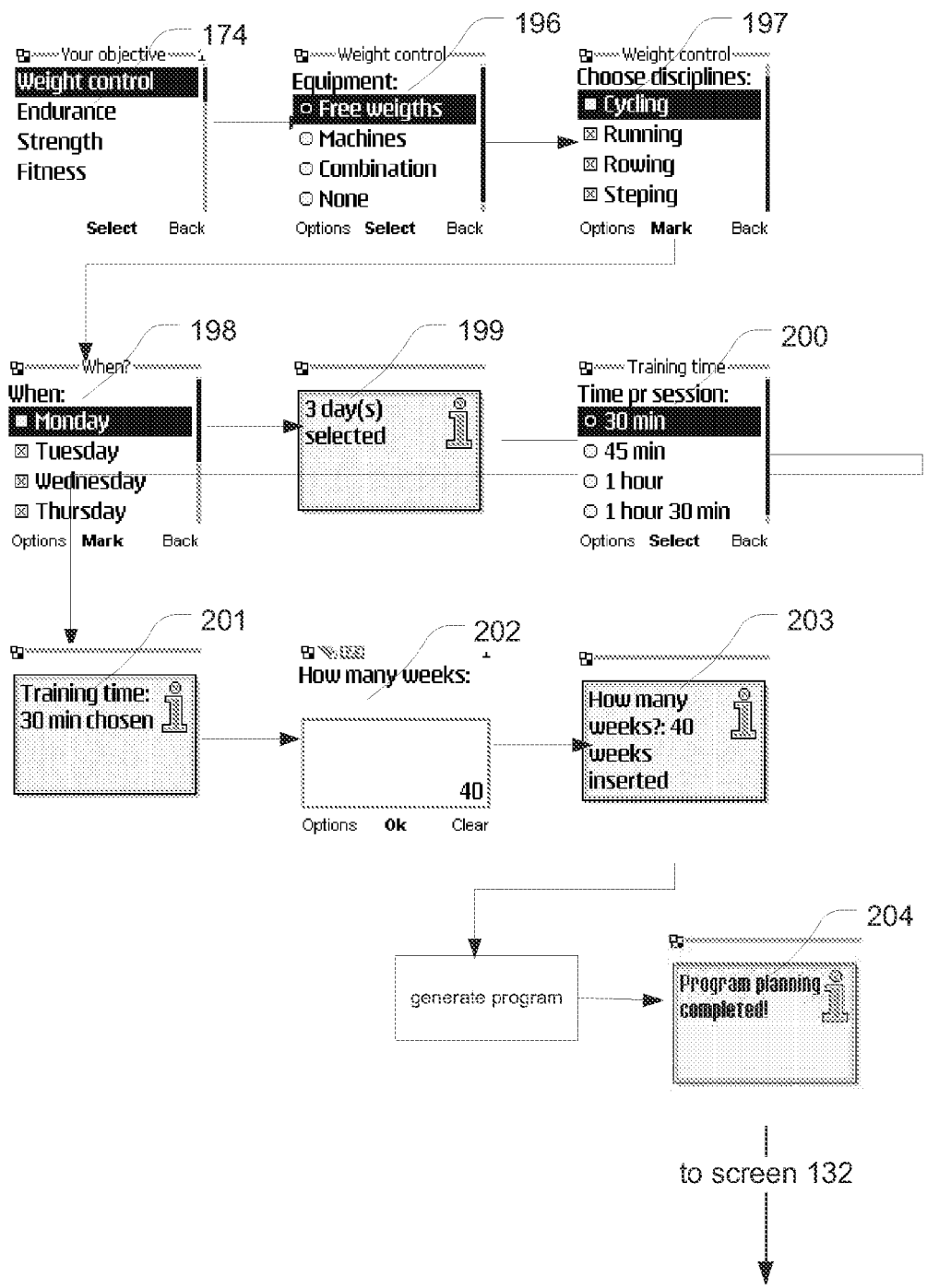
FIG. 20 illustrates the user interface of the MIDlet 35 for planning a weight control exercise program.

Referring to FIG. 20, if the user selects the Weight control option from the program type list screen 174, the user is presented with an equipment selection list screen 196 which enables to user to specify the equipment, if any, that the user wishes to use.

After the user has made their equipment selection, a discipline selection list screen 197 is displayed so that the user can select the discipline that they wish to perform during their new program. In the present example, the options available are Cycling, Running, Rowing, Stepping and Swimming.

After the user has selected a discipline from the discipline selection list screen 197, the MIDlet 35 then displays a weekday multiselect list screen 198 which enables a user to identify the days of each week on which they are to exercise. Only 2 to 4 days may be selected for exercising in each week by a low endurance user and only 2 to 5 days by other users. The number of days selected is then displayed in a days confirmation screen 199 which is displayed for a short period.

A session time list screen 200 is then displayed to enable the user to select an exercise session length from among 30, 45, 60 and 90 minutes. Low endurance users cannot select 90-minutes for the session length. The selected exercise session length is confirmed by a session length confirmation screen 201 which is displayed for a short period.

Next, the user is presented with a weeks entry screen 202 which enables the user to enter the number of weeks that the program is to run for. The entered number of weeks must be in the range 5 to 50. The entered number of weeks is confirmed in a weeks confirmation screen 201 which is displayed for a short period.

When the number of weeks has been confirmed, the MIDlet 35 generates the weight control exercise program for the user.

Figure 21:
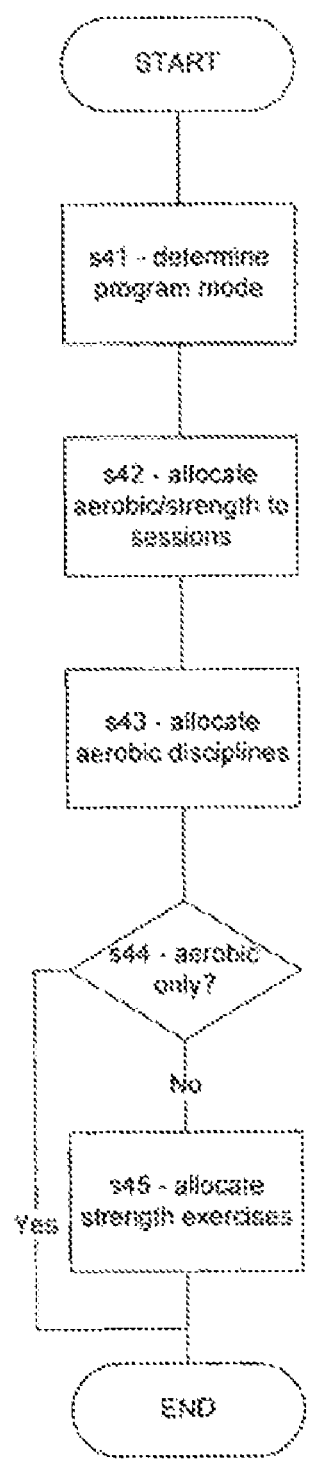
FIG. 21 is a flowchart illustrating generation of a weight control exercise program.

Referring to FIG. 21, the MIDlet 35 first determines a mode for the program in dependence on the number of sessions per week and the session length entered by the user and the user's endurance level with reference to the data in Tables 13 and 14 below.

TABLE 14

| | | Session Length | | | |
|---|---|---|---|---|---|
| Endurance | Sessions | 0.5 | 0.45 | 1 | 1.5 |
| LOW | 2 | 1 | 5 | 9 | |
| | 3 | 1 | 5 | 9 | |
| | 4 | 1 | 6 | 10 | |
| MODERATE | 2 | 1 | 5 | 9 | 12 |
| | 3 | 1 | 5 | 9 | 12 |
| | 4 | 1 | 6 | 10 | 13 |
| | 5 | 3 | 7 | 10 | 13 |

TABLE 15

| Mode | Exercise Mix |
|---|---|
| 1 | 30 min aerobic exercise |
| 3 | 2 × 30 min strength + 3 × 30 min aerobic exercise |
| 5 | 45 min aerobic exercise |
| 6 | 2 × (45 min aerobic exercise + 45 min strength switching) |
| 7 | 2 × 45 min strength + 3 × 45 min aerobic exercise switching |
| 9 | 30 min aerobic exercise + 30 min strength |
| 10 | 30 min aerobic exercise + 30 min strength split |
| 12 | 60 min aerobic exercise + 30 min strength |
| 13 | 45 min aerobic exercise + 45 min strength split |

The mode number is obtained from Table 14 and the aerobic/strength exercise mix is obtained from Table 15. Aerobic, i.e. endurance, exercising and strength exercising are allocated to sessions in accordance with Table 15. For instance, if mode 1 is used, all sessions are aerobic. However, if mode 6 is used, 45 minute sessions alternate between aerobic and strength exercises.

The aerobic sessions are allocated disciplines in accordance with the Grade 1 (Wellbeing) section of Table 7 and Table 8 above (step s43).

Considering now, by way of example, a person who has moderate endurance and has selected four sessions per week over 10 weeks, cycling and machines, Table 14 give use exercise mode 6 and Table 15 indicates that this comprises alternating sessions of aerobic and strength exercise. Thus, there are 20 sessions that need to be filled with 7 (33%) class a sessions, 6 (32%) class b sessions, 4 (20%) class c sessions and 3 (15%) class d sessions.

The sessions are allocated classes by the algorithm described above with reference all but the last week of an endurance program. Thus, in the present example, the sessions are allocated classes as shown in FIG. 22.

If the mode includes strength sessions (step s44), sculpturing exercises are allocated to the strength sessions in accordance with Tables 9 and 10 and the allocation algorithm described above with reference to generation of a strength exercise program.

In the case of the present example, exercise category 6 would be obtained from Table 10. Assuming that exercise combination 6.1 was selected at random from combinations 6.1 and 6.2, each strength session will need to include exercises chest 1, back 1, shoulders 1, triceps 1, biceps 1, chest 2 and back 2 as defined in Table 11. Consequently, the strength sessions (the even sessions in FIG. 22), may comprise: chest presses, pull downs, shoulder presses, one arm extensions, preacher curls, cable crosses and seated rowing.

The completed program is saved in the MIDlet's record store.

If the user selects the Fitness option from the program type list screen 174, the user progresses through the same sequence of screens as when Weight control is selected. The only difference in the screens themselves is that the title is "Fitness" instead of "Weight control". The generation of fitness programs is substantially the same as the generation of weight control programs. However, the mode is determined in accordance with Table 16 below.

TABLE 16

|  |  | Session Length | | | |
| --- | --- | --- | --- | --- | --- |
| Endurance | Sessions | 0.5 | 0.45 | 1 | 1.5 |
| LOW | 2 | 1 | 5 | 9 |  |
|  | 3 | 1 | 5 | 9 |  |
|  | 4 | 2 | 6 | 10 |  |
| MODERATE | 2 | 1 | 5 | 9 | 12 |
|  | 3 | 1 | 5 | 9 | 12 |
|  | 4 | 1 | 6 | 10 | 13 |
|  | 5 | 3 | 7 | 10 | — |
| HIGH | 2 | 1 | 5 | 9 | 12 |
|  | 3 | 1 | 6 | 9 | 12 |
|  | 4 | 2 | 6 | 10 | 13 |
|  | 5 | 3 | 7 | 10 | — |
|  | 6 | 4 | 8 | 11 | — |

Table 16 also indicates the session number and duration combinations that are allowed for users having different endurances.

The mode definitions for fitness programs are set out in Table 17 below.

TABLE 17

Mode Exercise Mix

| 1 | 30 min aerobic training |
| --- | --- |
| 2 | 30 min aerobic training and 30 min strength (switching) |
| 3 | 2 × 30 min strength + 3 × 30 min aerobic training |
| 4 | 3 × 30 min strength + 3 × 30 min aerobic training |
| 5 | 45 min aerobic training |
| 6 | 45 min aerobic training + 45 min strength switching |
| 7 | 3 × 45 min strength + 2 × 45 min aerobic training switching |
| 8 | 3 × 45 min strength + 3 × 45 min aerobic training switching |
| 9 | 30 min aerobic training + 30 min strength |
| 10 | 30 min aerobic training + 30 min strength split |
| 11 | 3 × 60 min strength + 3 × 60 min aerobic training |
| 12 | 45 min aerobic training + 45 min strength |
| 13 | 45 min aerobic training + 45 min strength split |

The process of allocating exercises to sessions for a fitness program is the same as that described above for a weight control process.

The completed program is saved to the MIDlet's record store.

If the user selects the Start Planned option from the main screen 132, the MIDlet 35 performs a process 135 to guide the user through an exercise session of the current plan.

Figure 23:
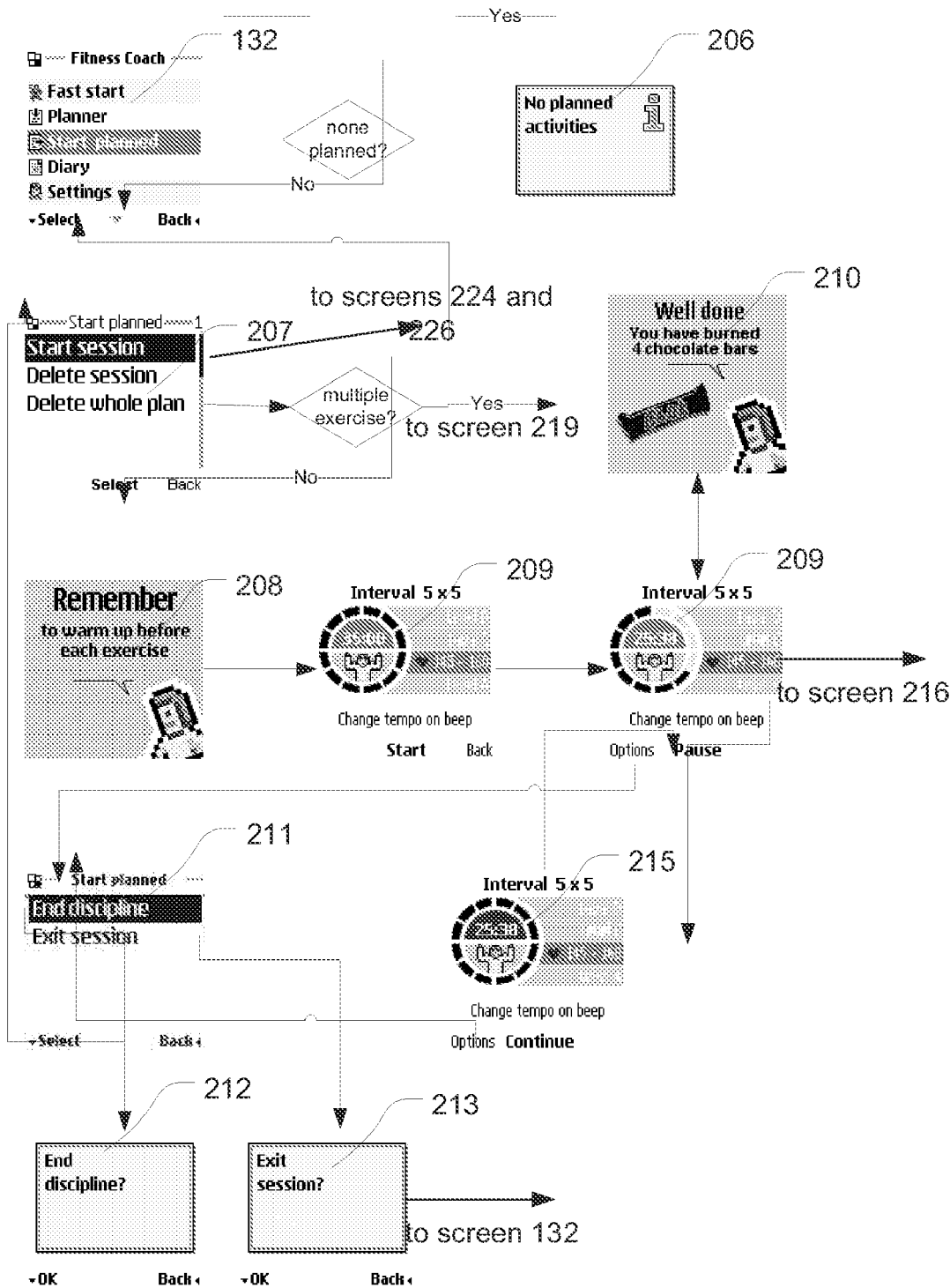
FIG. 23 illustrates the user interface of the MIDlet 35 for an planned exercise session.
Figure 23:
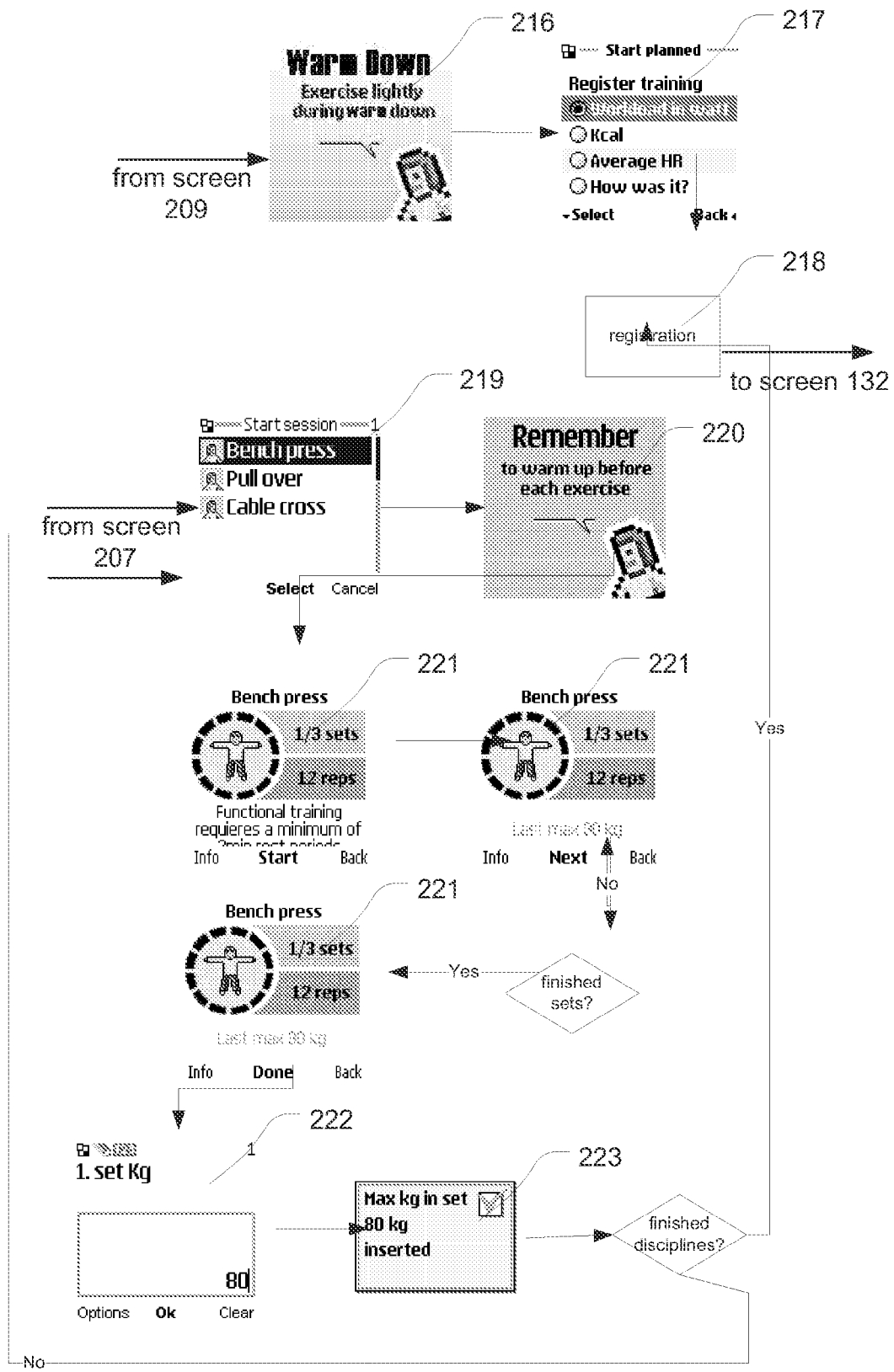
Figure 23:
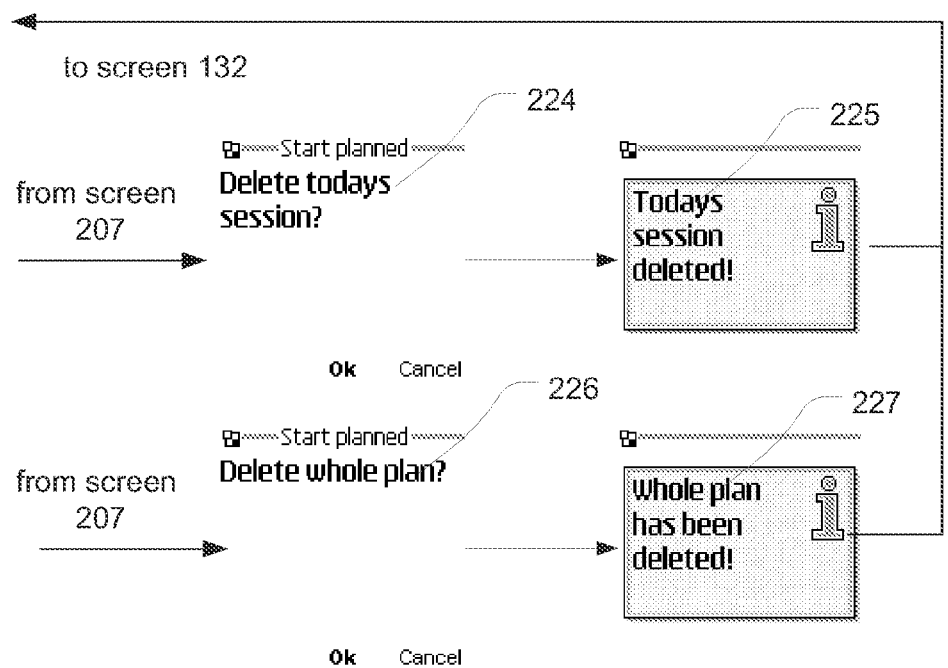

Referring to FIG. 23, when the Start Planned option has been selected, it is determined whether there is a pending exercise session for the current day. If there is not a pending session, the user is informed of this by a no session information screen 206, which is displayed for a short period before the display returns to the main screen 132.

If, however, there is a pending session, the user is presented with a session options list screen 207. The user can choose to start the pending session, delete the pending session or delete the entire program from the session options list screen 207.

If the user chooses to start the pending session, it is determined whether the session comprises a plurality of exercises. If the session consists of only one exercise, the parameters of the session are determined. The activity is obtained from the stored data defining the current plan. The default activity length is obtained from the Table 8 information and multiplied by factor representing the user's endurance level/1000. The factor is initially 1 for a low endurance person, 1.4 for a moderate endurance person and 1.7 for a high endurance person. As will be explained below, the user's endurance may be modified as the user progresses through a program. The pattern of intervals and pauses, if any is also obtained from the Table 8 information. Enough information is now available for the user to be guided through the session.

When the activity information has been obtained, the user is presented with an information screen 208, reminding the user to warm up before exercising, which then gives way to an exercise guidance screen 209. The exercise guidance screen 209 is generally arranged as shown in FIG. 12 but contains information relevant to the current session.

When the user selects the Start command from the exercise guidance screen 209, the MIDlet 35 begins timing the user's performance of the current session's activity. During this period, the MIDlet 35 occasionally displays motivational messages in motivational message screens 210. For instance, a motivational message may inform a user of a foodstuff that has a calorific value corresponding to the amount of energy notionally produced by the user while performing the discipline. The motivational message screens 210 are displayed for a short period before the display reverts to the exercise guidance screen 209. The MIDlet 35 also generates audio signals and updates the exercise guidance screen 209 to inform the user when to pause or vary their activity in the cases of interval and fartlek exercises.

If the user selects Options from the exercise guidance screen 209, the user is presented with an options menu 211 comprising End discipline and Exit session options. If the user selects the End discipline option, the user is presented with an end discipline confirmation screen 212 and, if the user confirms that the discipline is to be ended, the MIDlet 35 stops timing and displays session options list screen 207 again. The discipline is not recorded as having been completed.

If the user selects the Exit session option, the user is presented with an exit session confirmation screen 213 and, if the user confirms that the discipline is to be ended, the MIDlet 35 stops timing and displays the main screen 132 again.

If the user selects the Pause command from the exercise guidance screen 209, the user is presented with a paused discipline screen 215. The MIDlet's timing of the discipline is paused while the paused discipline screen 215 is being displayed. When the user selects the Continue command from the paused discipline screen 215, the MIDlet 35 restarts its timing operation and displays the exercise guidance screen 209 again. The user can also end the current discipline or exit the current session by selecting the Options from the paused discipline screen 215 which takes the user to the options menu screen 211.

When the period calculated for the current discipline has elapsed, allowing for any pauses, the MIDlet 35 displays a discipline completed screen 216, which advises the user to warm down, for a short period. The MIDlet 35 also produces an audible indication that the set period has elapsed. The discipline completed screen 216 is replaced with a registration list screen 217 is displayed.

From the user's perspective the registration process 218 is as described above in the context of the fast start process 133. It differs in that the MIDlet 35 adds the points gained to a local record of the user's process through the program.

If it is determined that the current session comprises a plurality if disciplines, the user is presented with a discipline list screen 219 which consists of the disciplines that the user must perform in the current session. The user can now select the first discipline to be performed. In the present example, the disciplines are Bench press, Pull over and Cable cross and the user has selected Bench press. Icons beside the elements in the discipline list screen 219 indicate whether the disciplines have been not been started, have been completed or have been interrupted.

On selecting the starting discipline, the user is presented for a short period with an information screen 220 which reminds the user to warm up before exercising. The information screen 220 is replaced by a exercise guidance screen 221.

Figure 24:
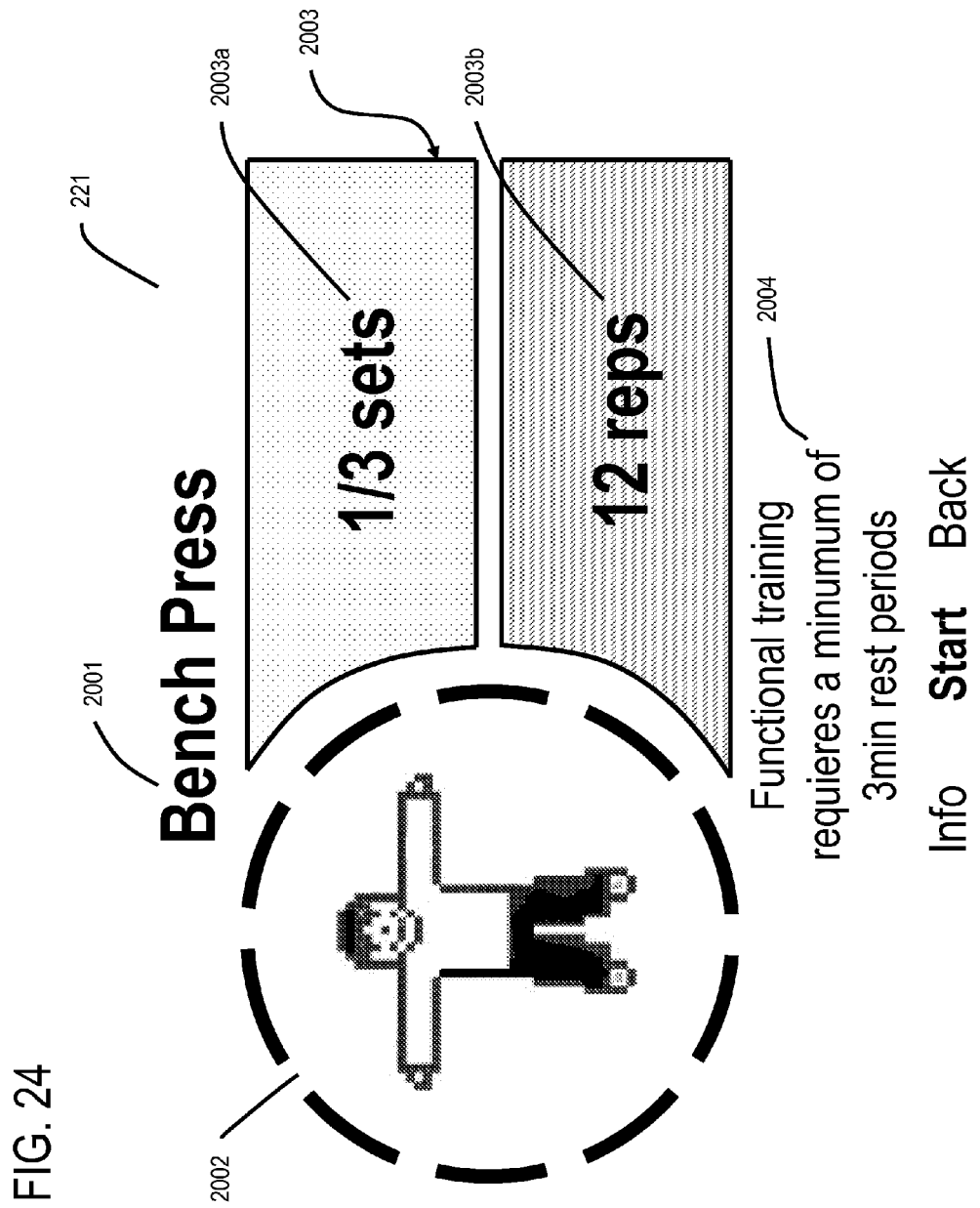
FIG. 24 shows another exercise guidance screen of the MIDlet's user interface.

Referring to FIG. 24, the exercise guidance screen 221 comprises a title 2001, an exercise themed graphic 2002, an discipline progress section 2003 and a scrolling instruction section 2004. The title 2001 states the discipline. The discipline progress section 2003 comprises two sections 2003a, 2003b which display the progress through the current discipline in terms of sets and the number of reps in current set respectively The instruction section 2004 provides additional guidance and explanation to the user.

Referring back to FIG. 23, the details of the selected discipline are obtained from Table 18 below which defines the patterns of reps forming sets as a function of progress through a program and program type, i.e. sculpturing or functional training.

TABLE 18

| Weeks | 1-5 | 6-10 | 11-15 | 16-20 | 21-25 | 26-30 | 31- |
|---|---|---|---|---|---|---|---|
| Sculpturing (s) | | | | | | | |
| 3 sets | 3 ×12 | 3 × 10 | 3 × 8 | 12, 6, 12 | 6, 9, 12 | 12, 9, 6 | 12, 8, 12 |
| 4 sets | 4 × 12 | 4 × 10 | 4 × 8 | 12, 6, 6, 12 | 6, 8, 10, 12 | 8, 8, 12, 12 | 12, 8, 8, 12 |
| Functional (f) | | | | | | | |
| 3 sets | 3 × 6 | 3 × 5 | 3 × 4 | 3 × 3 | 6, 3, 6 | 6, 4, 2 | 5, 2, 5 |
| 4 sets | 4 × 6 | 4 × 5 | 4 × 4 | 4 × 3 | 6, 3, 3, 6 | 2, 4, 6, 6 | 4, 2, 2, 6 |
| Abs, lower back | | | | | | | |
| 3 sets | 3 × 20 | | | all weeks | | | |
| 4 sets | 4 × 20 | | | | | | |

When the user selects the start option from the exercise guidance screen 221, the main command changes from Start to Next and the information section 1004 displays the maximum weight lifted from the preceding session. When the user has completed the first set of reps, the user selects the Next command and the exercise guidance screen 221 is updated to indicate the current set and the number of reps in the current set. The user keeps performing the sets of reps and selecting the Next command until all of the sets have been completed. When all of the sets have been completed, the exercise guidance screen 221 is updated so that the Next command is replaced with a Done command. When the user selects the Done command, a maximum weight entry screen 222 which enables the user to enter the maximum weight lifted in the current session so that it can be recorded. The entered weight is confirmed in a weight confirmation screen 223 is displayed for a short period. Then, if there are still disciplines to perform, the discipline list screen 219 is displayed again. Otherwise, the registration process is joined at screen 164, which in this case does not refer to points but provides a summary of the weights lifted.

If the user selects the Delete session option from the session options list screen 207, a delete session screen 224 is displayed. If the user confirms that the current session should be deleted, the current session is marked as completed without any record of performance, i.e. points or weights, and a delete session confirmation screen 225 is displayed for a short period before the display reverts to the main screen 132.

If the user selects the Delete whole plan option from the session options list screen 207, a delete whole plan screen 224 is displayed. If the user confirms that the current plan should be deleted, the data defining the current plan is erased and a delete whole plan confirmation screen 225 is displayed for a short period before the display reverts to the main screen 132.

As a programs having an endurance element progress, the user's performance is monitored by reference to the accumulated points. More particularly, after every five weeks, the user's endurance level is adjusted.

Figure 25:
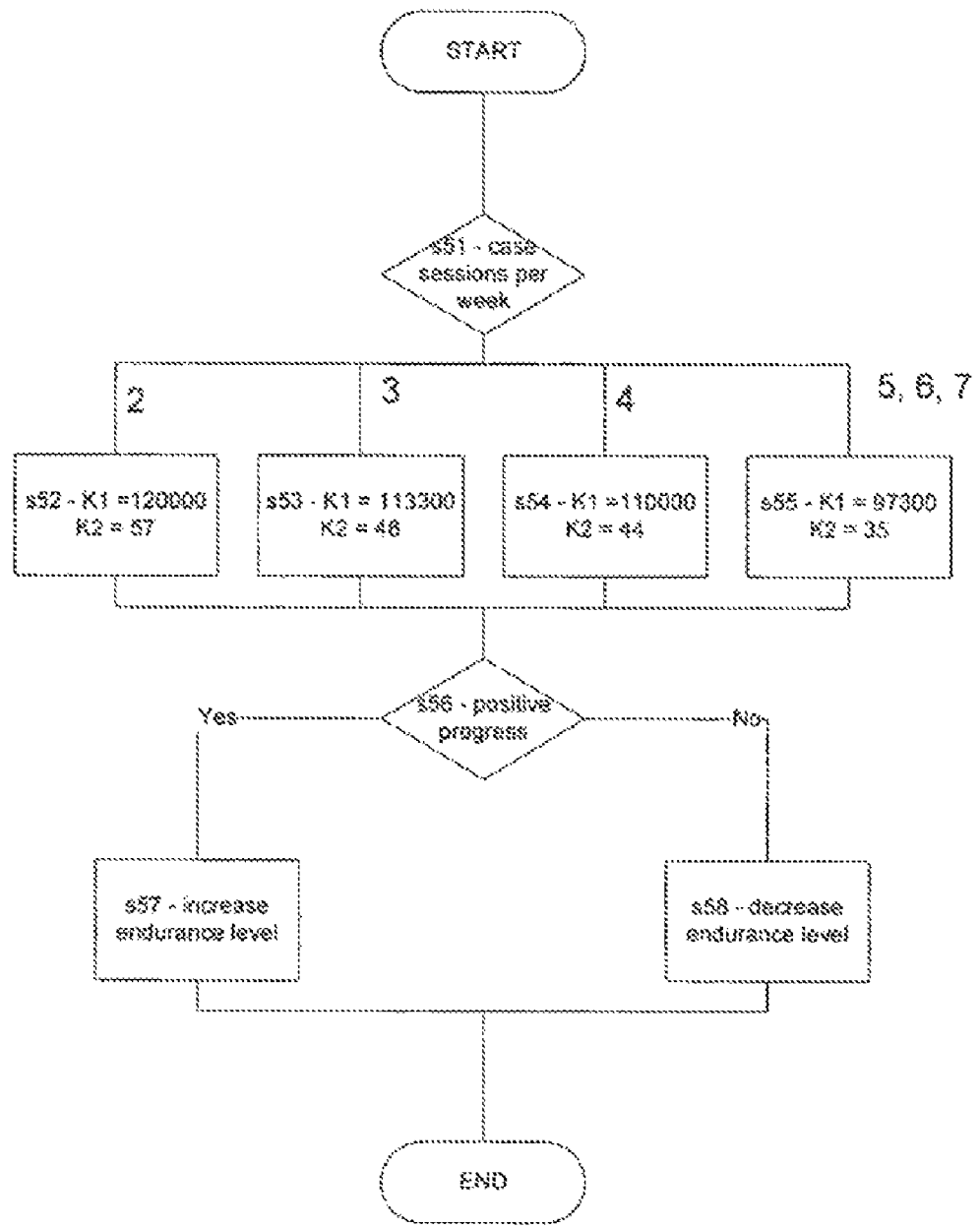
FIG. 25 is a flowchart of a method for adjusting a value representing a user's endurance.

Referring to FIG. 25, in order to adjust the user's endurance level, it is determined whether the number of sessions per week in the current plan is 2, 3, 4 or one of 5, 6 or 7 (step s51). Two variables, K1 and K2, are then set in dependence on the number of sessions per week (steps s52 to s55). It is the determined whether the user has made progress by comparing the accumulated points in the preceding five weeks with a target value, equivalent to 60% the theoretical maximum performance calculated from the user's personal data and additional data (step s56). If progress is being made, the user's endurance level is increased according to the formula:

$$\text{new endurance level} =$$
$$\text{old endurance level} + \frac{(K1 - K2 \times \text{old endurance level})}{1000}$$

However, if the user is performing poorly, their endurance level is reduced according to the formula:

$$\text{new endurance level} =$$
$$\text{old endurance level} + \frac{(475 + 1000 \times \text{old endurance level} - K1)}{1000 - K2}$$

The new endurance level is then used for setting the periods for which disciplines must be performed.

If the user's performance is substantially at odds with the expected performance, a screen may be displayed suggesting that the users endurance in the user's personal data be changed up or down as necessary.

If the user selects the Diary option from the main screen 132, a diary process 136 is performed.

Figure 26:
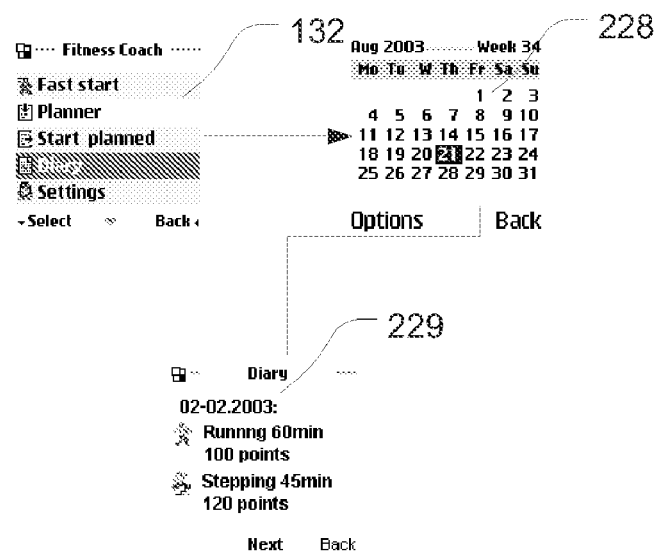
FIG. 26 illustrates the user interface of the MIDlet 35 for its diary function.

Referring to FIG. 26, selecting the Diary option from the main screen 132 causes a calendar screen 228 to be displayed. The calendar screen 228 has an option menu comprising View and Update options. Selecting the View option causes a detail screen 229 to be displayed. The detail screen 229 includes detail of any sessions on the day currently selected in the calendar screen 228 and other date-specific information. Selecting the Update option causes the mobile phone 2 to request update information from the server 3. The update information may comprise information about forthcoming events that may be of interest to the user.

If the user selects the Information option, the user is provided with information about the MIDlet 35 and more generally about exercise and fitness.

Figure 27:
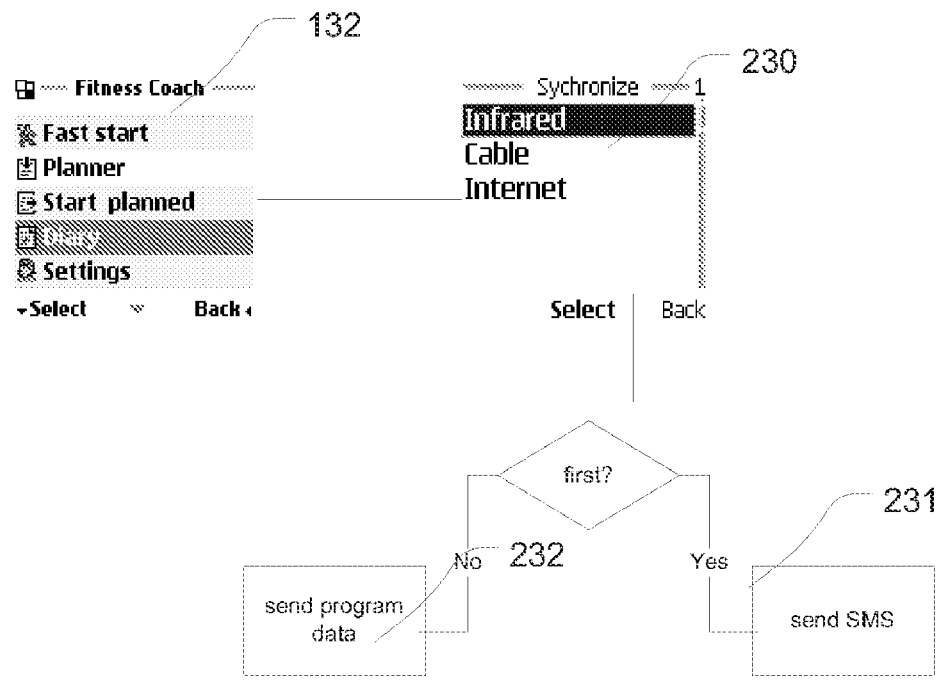
FIG. 27 illustrates the user interface of the MIDlet 35 for its synchronization function.

Referring to FIG. 27, if the user selects the Synchronization option, the user is presented with a synchronization screen 230. The user can opt to transfer data to a personal computer using a cable or infrared link (not shown). The user can also opt to transmit data to the server 3 via the Internet 5. On the first occasion that the Internet option is selected, the MIDlet 35 causes the mobile phone 2 to send 231 a registration SMS message to the server 3. The user then receives a reply SMS message in the normal manner. The reply message includes a username and password for accessing the server 3. On subsequent occasions, selecting the Internet option results in data being transmitted 232 to the server 3.

The data transmitted in the synchronization process 138 is an XML document comprising a definition of the current program and a record of the user progress with the current program.

Figure 28:
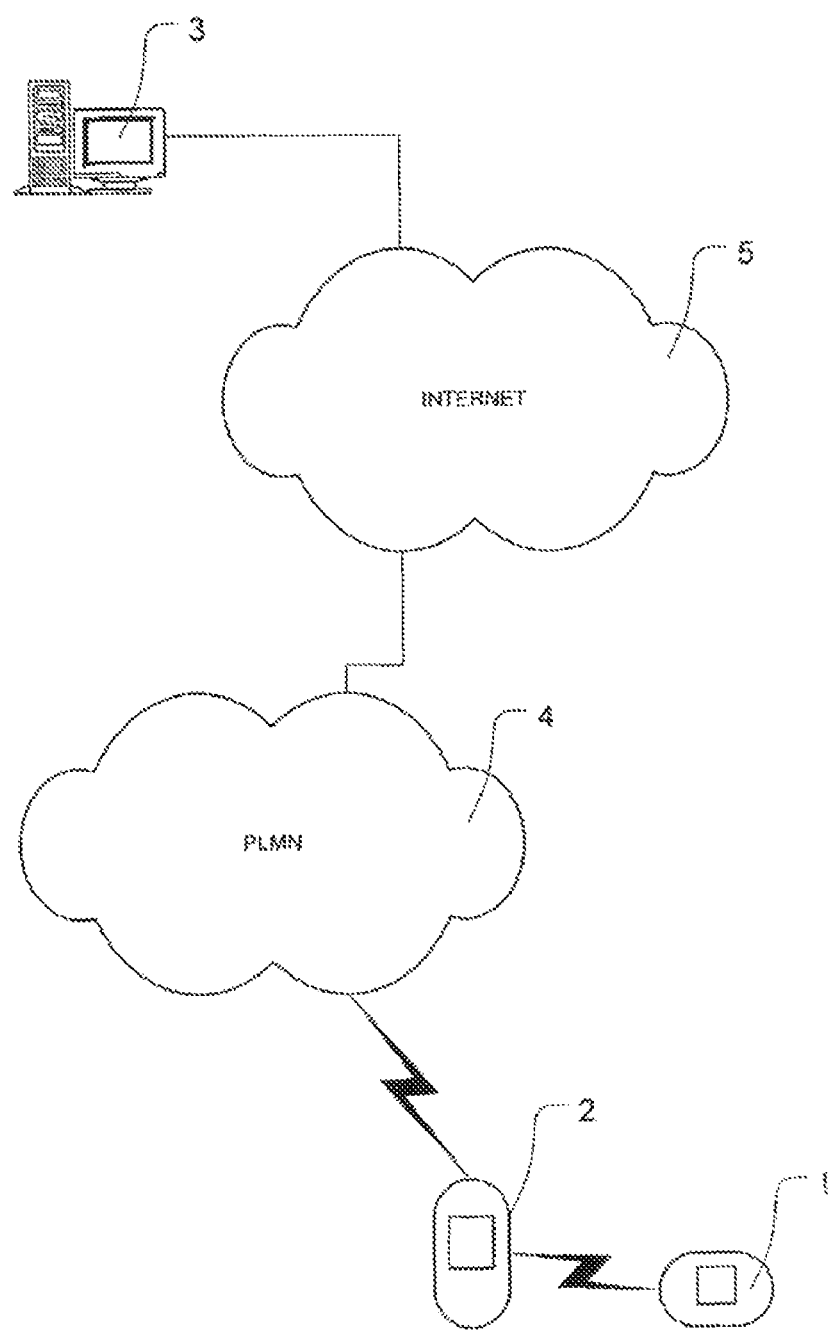
FIG. 28 shows the major components of a second exemplary system embodying the present invention.

Referring to FIG. 28, the second exemplary system comprises an activity monitor 1, a mobile phone 2 and a server 3. The activity monitor 1 can monitor the movement of a user and derive a value for the energy expended by the user while performing the monitored movement. The mobile phone 2 and the activity monitor 1 can communicate with each other using infrared signalling. Other wireless techniques, e.g. WiFi and Bluetooth, or wired techniques may be used instead of infrared signalling.

The mobile phone 2 can communicate with the server 3 via a mobile phone network 4 and the Internet 5 using xml messages and the HTTP protocol. The mobile phone 2 supports J2ME (Java 2 Micro Edition) MIDlets and the fitness program functions of the mobile phone 2 are implemented by a MIDlet.

The activity monitor 1 can be conveniently worn on the person during exercise.

The server 3 is a conventional HTTP server such as Apache.

Figure 29:
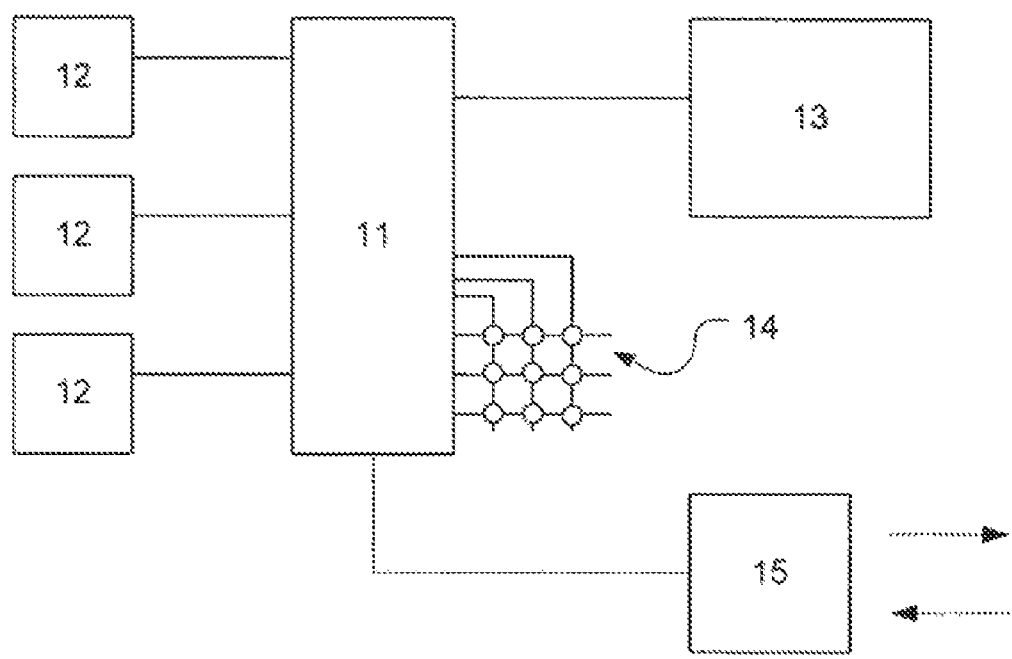
FIG. 29 is a block diagram of the activity monitor of FIG. 27.

Referring to FIG. 29, the activity monitor 1 comprises a microcontroller 11, a plurality of accelerometers 12 sensitive to movement in mutually orthogonal directions, a display 13, buttons 14 for enabling a user to control the activity monitor 1 and an infrared transceiver 15. The outputs of the accelerometers 12 are connected to analog-to-digital converter inputs of the microcontroller 11 which is configured to calculated energy expenditure and distance traveled (pedometer function) therefrom.

The buttons 14 arranged electrically in a matrix which is continually scanned by the microcontroller 11 in order to detect the buttons 14 being pressed by the user. The display 13 is connected to output pins of the microcontroller 11 and is controlled by the microcontroller 11 to display information relating to a current activity and to provide feedback to the user when the user is setting up the activity monitor 1.

The infrared transceiver 15 is coupled to a serial port of the microcontroller 11 for bidirectional communication with the mobile phone 2.

The microcontroller 11 is responsive to pressing of the buttons 14 for the input of user data, comprising the user's name, date of birth, height, weight and sex. This information enables the monitor to calculate the energy expended by the user during a sensed activity, for starting and stopping sensing and for communication with the mobile phone 2.

The MIDlet 35 of the second embodiment differs from that of the first embodiment in that the registration process can accept energy expended per minute data wirelessly from the activity monitor in addition to the manual methods described above. Points are derived from the wirelessly received data in accordance with Equation 2 and Tables 2 and 3 above.

Figure 30:
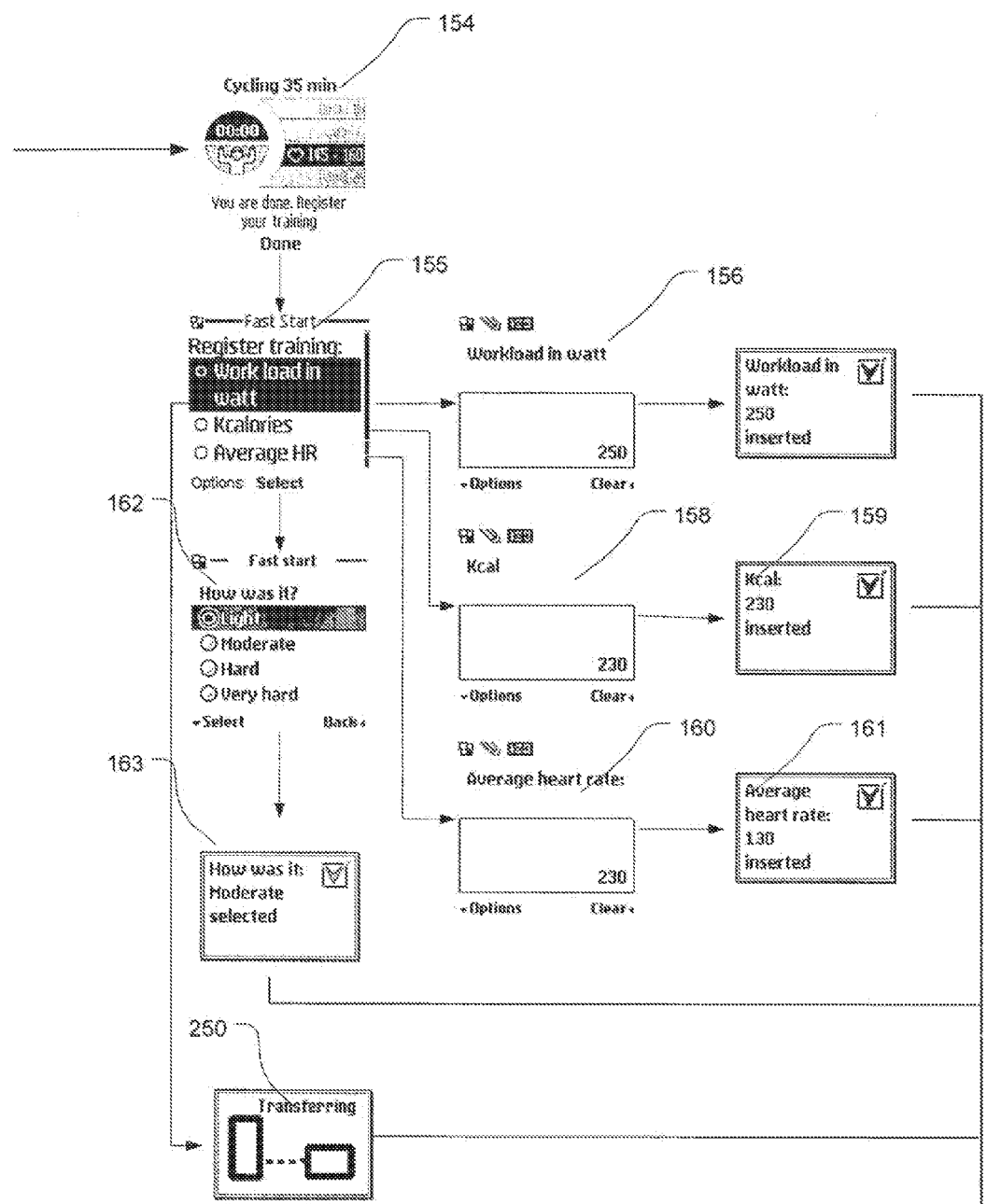
FIG. 30 illustrates the user interface of the MIDlet 35 of the second exemplary system during exercise registration.

Referring to FIG. 30, during registration, the registration list screen 155 includes an additional Wireless option. If the user selects the Wireless option, the mobile phone 2 is put into a state in which it can receive performance data from the activity monitor 2. During communication, the MIDlet 35 31 displays a communication information screen 250.

The energy expended is transmitted from the activity monitor 1 to the mobile phone 2 in a data package.

Figure 31:
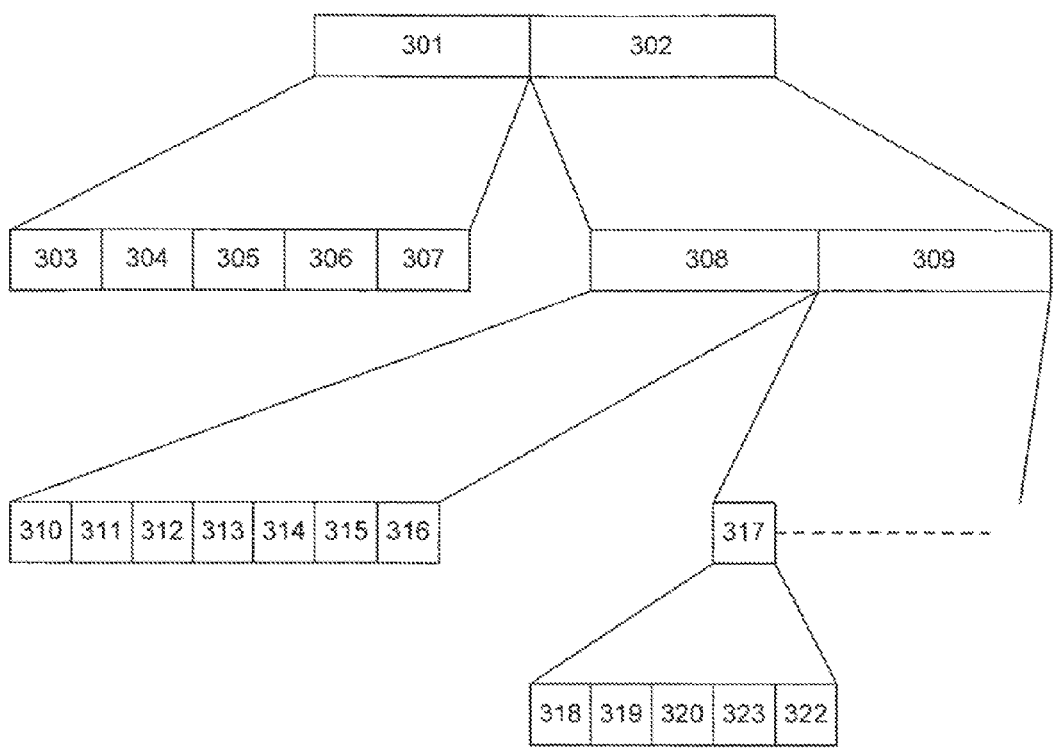
FIG. 31 illustrates the structure of a data package according to the present invention.

Referring to FIG. 31, the data package 300 comprises a package header 301 and a package body 302. The package header 301 comprises version 303, package length 304, time 305, final flag 306 and command 307 fields. The version field 303 is 1 byte and can be a value from 0 to 255. The package length field 304 is 2 bytes and occupies bytes 5 and 6 of the package. The time field 305 is a 32-bit time stamp. The final flag field 306 is bit 7 of a byte and the command field 307 is bits 0 to 6 of the byte containing the final flag field 306. The final flag field 306 is set to 1 to indicate a final package.

The package body 302 comprises a personalized fitness settings section 308 and a fitness entry collection section 309.

The fitness setting section 308 comprises an activity monitor ID field 310, a settings last modified time field 311, a name field 312 containing the user's name, a date of birth field 313, a height field 314, a weight field 315 and a sex field 316. The activity monitor ID field 310 comprises a two-byte integer. The settings last modified time field 311 is a 32-bit time stamp. The name field 313 comprises ten bytes and holds the user's name. The date of birth field 313 holds the user's date of birth in 8-bytes in YYYYMMDD format. The height field 314 holds the user's height in centimeters in one byte. The weight field 315 holds the user's weight in kilograms in two bytes. The sex field 316 uses one bit to indicate female (0) or male (1).

The fitness entry collection section 309 comprises one or more fitness entries 317 which contain information relating to different disciplines within a session. Each fitness entry 317 comprises a time field 318, an activity type field 319, a kilocalories per minute field 320, a duration field 321 and a distance field 422. The time field 318 is a 32-bit time stamp indicating when the discipline was performed. The activity type field 319 comprises one byte and indicates which discipline was performed. The kilocalories per minute field 320 comprises 1 byte and indicates the average energy expended per minute during performance of the discipline. The duration field 321 comprises two bytes and indicates the duration of the performance of the discipline by the user. The distance field 322 comprises two bytes and indicates the distance traveled by the user obtained from the pedometer function of the activity monitor.

The short periods mentioned in the foregoing description of the MIDlet user interface are preferably in the range 1 to 5 seconds and may vary from one screen to another.

It will be appreciated that the present invention may be implemented in may different ways. For example, the program generation may be performed at a server and downloaded to a mobile phone or other apparatus, either as a complete plan or session by session. The software of the mobile phone or other apparatus may be substantially limited to providing a user interface to processes running on a remote computer, with which it communicates using some form of remote procedural calls, e.g. CORBA, XML-RPC or SOAP. The other device could comprise computers built into exercise machines which can provide the user interface, e.g. a web pages provided by a remote server and displayed in a browser. The user can then have the user interface available as the user moves from machine to machine to perform different disciplines of a session.

The role of the mobile phone may be taken by any convenient processing device, e.g. a PDA or a personal computer.

The embodiments described above use MIDlets for convenience. However, the controlling software need not be a MIDlet.

The software may be provided by an electrical or electromagnetic signal comprising program codes, e.g. a MIDlet 35 jar file. Software provided in this way can be used for controlling a processing device for implementing an embodiment of the present invention. A recording of such a signal may be carried on or in a data carrier, e.g. a DVD-ROM, a CD-ROM or a memory card.

What is claimed is:

1. A method, comprising facilitating a processing of and/or processing (1) data and/or (2) information and/or (3) at least one signal, the (1) data and/or (2) information and/or (3) at least one signal based, at least in part, on the following:
    a generating, at a mobile phone, of an exercise program based, at least in part, on one or more physical parameters input by a user via a user interface;
    a controlling of the user interface so as to provide guidance to a user during performance of the exercise program; and
    a controlling of the user interface so as to display a plurality of fitness disciplines, wherein one or more of the plurality of fitness disciplines may be selected by the user via the user interface.

2. A method according to claim 1, wherein the (1) data and/or (2) information and/or (3) at least one signal are further based, at least in part, on the following:
    an aerobic fitness value for the user based on physiological information input by the user.

3. A method according to claim 2, wherein at least one of the plurality of fitness disciplines is associated with a variable exercise duration parameter, and wherein the (1) data and/or (2) information and/or (3) at least one signal are further based, at least in part, on the following:
    a setting of the variable exercise duration parameter on the basis of the physiological information input using the input device.

4. A method according to claim 3, wherein the physiological information comprises information relating to aerobic fitness for the user.

5. A method according to claim 3, wherein the (1) data and/or (2) information and/or (3) at least one signal are further based, at least in part, on the following:
    a calculation of a duration of the exercise program by multiplying a base duration by a value obtained from the aerobic fitness value for the user.

6. A method according to claim 5, wherein the (1) data and/or (2) information and/or (3) at least one signal are further based, at least in part, on the following:
    physiological information at the end of an exercise program for which guidance has been provided; and
    a modification of the aerobic fitness value in dependence on the physiological information input at the end of an exercise program for which guidance has been provided.

7. A method according to claim 6, wherein the (1) data and/or (2) information and/or (3) at least one signal are further based, at least in part, on the following:
    a modification of the aerobic fitness value at predetermined times.

8. A method according to claim 7, wherein the predetermined times are at intervals between the range of 3 to 8 weeks.

9. A method according to claim 7, wherein the modification of the aerobic fitness value comprises determining an expected performance, determining an actual performance from the physiological information received after the exercise program, comparing the expected performance and the actual performance, and increasing or decreasing the aerobic fitness value depending on a result of the comparison.

10. A method according to claim 2, wherein the (1) data and/or (2) information and/or (3) at least one signal are further based, at least in part, on the following:
    a generating of the exercise program based, at least in part, on different intensity classes, wherein ratios of the different intensities classes are determined by the aerobic fitness value.

11. A non-transitory computer-readable storage medium carrying one or more sequences of one or more instructions which, when executed by one or more processors, cause an apparatus to at least perform the following steps:
    generating, at a mobile phone, an exercise program based, at least in part, on one or more physical parameters input by a user via a user interface;
    controlling the user interface so as to provide guidance to a user during performance of the exercise program; and
    controlling the user interface so as to display a plurality of fitness disciplines, wherein one or more of the plurality of fitness disciplines may be selected by the user via the user interface.

12. A non-transitory computer-readable storage medium according to claim 11, wherein the apparatus is caused to further perform:

determining an aerobic fitness value for the user based on physiological information input by the user.

13. A non-transitory computer-readable storage medium according to claim 12, wherein at least one of the plurality of fitness disciplines is associated with a variable exercise duration parameter, and wherein the apparatus is caused to further perform:
   setting the variable exercise duration parameter on the basis of the physiological information input using the input device.

14. A non-transitory computer-readable storage medium according to claim 13, wherein the physiological information comprises information relating to aerobic fitness for the user.

15. An apparatus comprising:
   at least one processor; and
   at least one memory including computer program code for one or more programs,
   the at least one memory and the computer program code configured to, with the at least one processor, cause the apparatus to perform at least the following,
      generate, at a mobile phone, an exercise program based, at least in part, on one or more physical parameters input by a user via a user interface;
      control the user interface so as to provide guidance to a user during performance of the exercise program; and
      control the user interface so as to display a plurality of fitness disciplines, wherein one or more of the plurality of fitness disciplines may be selected by the user via the user interface.

16. An apparatus according to claim 15, wherein the apparatus is further caused to:
   determine an aerobic fitness value for the user based on physiological information input by the user.

17. An apparatus according to claim 16, wherein at least one of the plurality of fitness disciplines is associated with a variable exercise duration parameter, and wherein the apparatus is further caused to:
   set the variable exercise duration parameter on the basis of the physiological information input using the input device.

18. An apparatus according to claim 17, wherein the physiological information comprises information relating to aerobic fitness for the user.

19. A method according to claim 17, wherein the apparatus is further caused to:
   calculate a duration of the exercise program by multiplying a base duration by a value obtained from the aerobic fitness value for the user.

20. An apparatus of claim 15, wherein the apparatus is a mobile phone further comprising:
   user interface circuitry and user interface software configured to facilitate user control of at least some functions of the mobile phone through use of a display and configured to respond to user input; and
   a display and display circuitry configured to display at least a portion of a user interface of the mobile phone, the display and display circuitry configured to facilitate user control of at least some functions of the mobile phone.

* * * * *